(12) United States Patent
Groseth

(10) Patent No.: US 10,485,985 B2
(45) Date of Patent: *Nov. 26, 2019

(54) IRRADIATION DEVICE

(71) Applicant: PHOTOCURE ASA, Oslo (NO)

(72) Inventor: Morten Groseth, Oslo (NO)

(73) Assignee: PHOTOCURE ASA, Oslo (NO)

( * ) Notice: Subject to any disclaimer, the term of this patent is extended or adjusted under 35 U.S.C. 154(b) by 12 days.

This patent is subject to a terminal disclaimer.

(21) Appl. No.: 15/985,214

(22) Filed: May 21, 2018

(65) Prior Publication Data

US 2018/0264283 A1 Sep. 20, 2018

Related U.S. Application Data

(63) Continuation of application No. 14/783,240, filed as application No. PCT/EP2014/057148 on Apr. 9, 2014, now Pat. No. 9,974,974.

(30) Foreign Application Priority Data

Apr. 9, 2013 (GB) .................................. 1306369.8

(51) Int. Cl.
*A61N 5/06* (2006.01)
*A61K 41/00* (2006.01)

(52) U.S. Cl.
CPC .......... *A61N 5/062* (2013.01); *A61K 41/0061* (2013.01); *A61N 5/0603* (2013.01);
(Continued)

(58) Field of Classification Search
CPC ........ A61K 41/0061; A61N 2005/0605; A61N 2005/0607; A61N 2005/0608;
(Continued)

(56) References Cited

U.S. PATENT DOCUMENTS 4,858,624 A 8/1989 Shihata
5,445,608 A 8/1995 Chen et al.
(Continued)

FOREIGN PATENT DOCUMENTS

DE 296 11 520 U1 9/1996
DE 10 2006 001 736 A1 7/2007
(Continued)

OTHER PUBLICATIONS

Allison, R.R., et al., "PD/PDT for Gynecological Disease: A Clinical Review", Photodiagnosis and Photodynamic Therapy (2005); vol. 2. pp. 51-63.

(Continued)

*Primary Examiner* — Lynsey C Eiseman
*Assistant Examiner* — Jonathan T Kuo
(74) *Attorney, Agent, or Firm* — Fox Rothschild LLP

(57) ABSTRACT

An irradiation device for insertion into an orifice of the body to provide photodynamic therapy comprises: a housing moulded from a resilient material and adapted to be fully inserted and secured in the orifice, the housing enclosing an LED lamp system 22 and a power source 41 for powering the LED lamp system 22; wherein the device is independently operational while located in the orifice; characterized in that: the housing comprises a first housing part 2 for holding the power source 41 and a second housing part 4 for holding the LED lamp system 22, the first and second housing parts 2, 4 being separable and being preferably formed separately from the LED lamp system 22; and in that the first housing part 2 consists of a chamber 6 for holding the power source 41 and an opening 26 into the chamber 6 is provided through a resilient opening part 8, wherein the chamber 6 is closed when the first housing part 2 is joined to the second housing part 4.

28 Claims, 5 Drawing Sheets

(52) U.S. Cl.
CPC .............. *A61N 2005/0605* (2013.01); *A61N 2005/0607* (2013.01); *A61N 2005/0608* (2013.01); *A61N 2005/0611* (2013.01); *A61N 2005/0632* (2013.01); *A61N 2005/0645* (2013.01); *A61N 2005/0651* (2013.01); *A61N 2005/0652* (2013.01)

(58) Field of Classification Search
CPC .... A61N 2005/0611; A61N 2005/0632; A61N 2005/0645; A61N 2005/0651; A61N 2005/0652; A61N 5/0603; A61N 5/062; A61N 5/06–2005/073; A61B 18/20–18/28
See application file for complete search history.

(56) References Cited

U.S. PATENT DOCUMENTS

| | | |
|---|---|---|
| 5,674,239 A | 10/1997 | Zadini et al. |
| 8,057,464 B2 | 11/2011 | Chen et al. |
| 8,292,935 B2 | 10/2012 | Neuberger et al. |
| 2003/0097122 A1 | 5/2003 | Ganz et al. |
| 2003/0232303 A1 | 12/2003 | Black |
| 2004/0043349 A1 | 3/2004 | Liao |
| 2004/0259949 A1 | 12/2004 | Klaveness et al. |
| 2005/0104059 A1 | 5/2005 | Friedman et al. |
| 2005/0239018 A1 | 10/2005 | Green et al. |
| 2006/0136013 A1 | 6/2006 | Sherman |
| 2007/0149903 A1 | 6/2007 | Nan |
| 2007/0259310 A1 | 11/2007 | Goodson et al. |
| 2007/0260231 A1 | 11/2007 | Rose et al. |
| 2007/0260295 A1 | 11/2007 | Chen et al. |
| 2008/0065003 A1 | 3/2008 | Neuberger et al. |
| 2009/0198173 A1 | 8/2009 | Samuel et al. |
| 2009/0319008 A1 | 12/2009 | Mayer |
| 2011/0190689 A1 | 8/2011 | Bennett et al. |
| 2011/0295186 A1 | 12/2011 | Klem |
| 2012/0215141 A1 | 8/2012 | Peddicord |
| 2013/0261385 A1 | 10/2013 | Zipper |

FOREIGN PATENT DOCUMENTS

| | | |
|---|---|---|
| EP | 1 138 349 A2 | 10/2001 |
| GB | 2360461 A | 9/2001 |
| GB | 2366734 A | 3/2002 |
| GB | 2370992 A | 7/2002 |
| JP | 68-010067 A | 1/1938 |
| JP | 60-19744 Y | 6/1975 |
| JP | 2002-065875 A | 3/2002 |
| WO | 1993/012836 A1 | 7/1993 |
| WO | 1996/028412 A1 | 9/1996 |
| WO | 1998/046130 A1 | 10/1998 |
| WO | 1999/019024 A1 | 4/1999 |
| WO | 2001/087416 A1 | 11/2001 |
| WO | 2002/009690 A2 | 2/2002 |
| WO | 2002/010120 A1 | 2/2002 |
| WO | 2003/033067 A2 | 4/2003 |
| WO | 2004/082736 A2 | 9/2004 |
| WO | 2004/096074 A2 | 11/2004 |
| WO | 2005/092838 A1 | 10/2005 |
| WO | 2006/103678 A2 | 10/2006 |
| WO | 2007/127894 A2 | 11/2007 |
| WO | 2007/130072 A2 | 11/2007 |
| WO | 2008/021692 A2 | 2/2008 |
| WO | 2008/084241 A2 | 7/2008 |
| WO | 2010/078929 A1 | 7/2010 |
| WO | 2010/142457 A1 | 12/2010 |
| WO | 2011/038310 A1 | 3/2011 |
| WO | 2012/004399 A1 | 1/2012 |

OTHER PUBLICATIONS

Jacques, et al., "PDT with ALA/PPIX is Enhanced by Prolonged Light Exposure Putatively by Targeting Mitochodria" SPIE Proceedings vol. 2972, Optical Methods for Tumor Treatment and Detection, ed. T. Dougherty, San Jose, CA, (Feb. 1997); 6 pgs.

Keefe, K.A. et al., "Photodynamic Therapy of High-Grace Cervical Intraepithelial Neoplasia with 5-Aminiolevulinic Acid", Lasers in Surgery and Medicine (2001); vol. 31, pp. 289-293.

Sandstrom, et al., "Ambient Fabrication of Flexible and Larger-Area Organic Light-Emitting Devices Using Slot-Die Coating", Nature Communications (2012); DOI: 10. 1038/ncomms2002. pp. 1-5.

Seshadri, et al., "Light Delivery Over Extended Time Periods Enhances the Effectiveness of Photodynamic Therapy", Cancer Therapy: Preclinical, Cancer Res (2008); vol. 14:9; pp. 2796-2805.

Soergel, et al., "Photodynamic Therepy of Cervical Intraepithelial Neoplasia with Hexaminolevulinate", Lasers. Surg. Med.: (2008); vol. 40; pp. 611-615.

IRRADIATION DEVICE

This invention relates to an irradiation device for insertion into an orifice of the body for providing photodynamic therapy of diseases, lesions and conditions thereof.

An example of an orifice of the body where photodynamic treatment is of benefit is the female reproductive system. Conditions affecting the female reproductive system are discussed below. Similar conditions, or conditions that respond to similar treatments, can arise in other orifices, such as the rectum, ear, mouth or nose.

The human papillomavirus (HPV) is a virus that can infect the skin and mucus membranes in humans. More than 100 different types of HPV have been identified. Several HPV types are transmitted through sexual activity and are pathogenic. HPV is estimated to be the most common sexually transmitted infection in the US. Several hundred million women worldwide are infected with HPV once in their life-time (~70%), with the highest prevalence, 20-30%, occurring in young women. These viruses can cause infections in the female reproductive system (i.e. the vulva, vagina, cervix, uterus, fallopian tubes and ovaries) and result in diseases and abnormalities affecting the female reproductive system such as genital warts, dysplasia and cancer of the vulva, vagina and cervix.

Cervical cancer is a life-threatening disease and is today the third most common cancer form among women world wide. Scientists agree that there is a strong correlation between the development of cervical cancer and HPV. Persistent HPV infection of the cervix may induce cell abnormalities including cervical intraepithelial neoplasia (CIN), also known as cervical dysplasia, resulting in precancerous lesions, and ultimately cervical cancer.

Fortunately mild cellular abnormalities including CIN1 have a high degree of spontaneous regression (>60%), and this is a condition that is normally only followed up by colposcopy. Moderate to severe CIN (CIN2 and CIN3) have a lower degree of spontaneous regression and a higher risk of progression. Patients with CIN2 and CIN3 are therefore conisized, usually by surgical procedures including diathermia, laser conisation and hysterectomy. The efficacy is about 90%, but side effects are disturbing, causing increased risk of bleeding, infection, stenosis, infertility and preterm labour.

If not treated, the precancerous cells will progress into more severe forms like carcinoma and neuroendocrine carcinoma. Treatment methods for cervical cancer are, as with most other cancer forms, dependent on the development stage of the disease. Treatment of early stage cervical cancer is normally various forms of surgery, while late stage cervical cancer is treated with surgery in combination with radiation therapy and chemotherapy. The most common chemotherapy of cervical cancer includes use of cisplatin. It is estimated that around 11,000 women a year will be diagnosed with cervical cancer, and that almost 4,000 will die from the disease. The degree of survival (over 5 years) depends on the stage of the disease and is, on average, above 50%.

Photodynamic therapy (PDT) is a therapeutic modality using a combination of light and a photosensitiser. A photosensitiser is administered to a patient in need of such photodynamic therapy and is taken up into cells. When illuminated, i.e. excited by light, at a suitable wavelength the photosensitiser or "PDT drug" reacts with tissue oxygen to form oxygen radicals that interact with cellular organelles including the mitochondria and cell membranes. These interactions cause cell necrosis or apoptosis (programmed cell death). PDT is today used clinically for the treatment of several diseases, including various skin diseases.

Typical products for use in skin PDT are Metvix® (Galderma, Switzerland) and Levulan® (Dusa Pharmaceuticals Inc, Wilmington, USA).

A range of photosensitisers are known from the scientific literature. One type of such compounds is per se phototoxic to target cells or species or have light emitting properties when exposed to light. Such compounds have a relatively large molecular weight and are often complex molecules like phthalocyanines, chlorines, porphyrins and psoralens. Another type of compound are photosensitiser precursors that per se are not phototoxic or light emitting, but form photosensitisers, e.g. endogenous porphyrins, in vivo. Such compounds are typically 5-aminolevulinic acid (5-ALA) and derivatives of 5-ALA like 5-ALA esters, and will be referred to hereafter as "precursors".

There are several scientific reports on clinical research related to PDT of the cervix including PDT of HPV, however, PDT is today not a clinically valuable method for therapy of CIN and other diseases/conditions of the cervix. This is due to the ineffective results of therapy and the cumbersome procedure which involves the patients staying supine for 3-5 hours and connected to an external light source. Thus, there is a need for improved methods for PDT of the cervix.

WO 2010/078929 discloses a device designed to be fully inserted and secured in an orifice of the body during treatment of a condition within the orifice, without requiring connection to an external power supply or light source during operation. The device is independently operable whilst it is within the orifice and hence can provide illumination for PDT without concurrent connection to any external device. The device is hence fully self-contained and forms an enclosed unit including both the light source and the power supply required for photodynamic procedures.

As described in WO 2010/078929, it was found that the use of a specific device, in combination with a photosensitiser or precursor, improves therapy of cervical cancer and other cervical diseases, lesions and conditions, especially those diseases, lesions and conditions caused by HPV infection. Similar improvements can be made in connection with photodynamic treatment of other conditions affecting the female reproductive system like for instance vulvar or vaginal intraepithelial neoplasia (VIN or VAIN) or vulvar and vaginal carcinomas. Further, similar improvements can be made in connection with PDT of cancerous or precancerous conditions or lesions of any other orifice of the human or animal body.

Unlike the other prior art devices, the device of WO 2010/078929 does not require the patient to remain at a medical facility during treatment. Rather, use of the device will often require only one visit to the medical facility, after which the patient is free to leave. Prolonged ongoing treatment can occur while the patient continues with his or her normal daily activities.

However, despite the considerable advances made by the device of WO 2010/078929 in terms of the treatments that can be provided and the comfort for the patient, problems remain in relation to manufacture of the device.

According to one aspect the present invention provides an irradiation device for insertion into an orifice of the body to provide photodynamic therapy, the device comprising: a housing moulded from a resilient material and adapted to be fully inserted and secured in the orifice, the housing enclosing an LED lamp system and a power source for powering the LED lamp system; wherein the device is independently operational while located in the orifice; characterised in that: the housing comprises a first housing part for holding the power source and a second housing part for holding the LED lamp system, the first and second housing parts being separable and preferably being formed separately from the LED lamp system; and in that the first housing part consists of a chamber for holding the power source and an opening into the chamber is provided through a resilient opening part, wherein the chamber is closed when the first housing part is joined to the second housing part.

The term "irradiation device" according to the invention means a device which is a light source, i.e. provides light or illumination or radiation in the form of light but no ionizing radiation such as x-rays or gamma rays. The terms "illumination", "irradiation", "radiation" and "light" are used interchangeably herein.

With this device the manufacturing of the device is improved compared to the prior art device of WO 2010/078929. The device of WO 2010/078929 has a housing that is moulded in a single piece enclosing the power source and LED lamp system. This has advantages in relation to the sealing of the device. However, the inventors have found that with the arrangement of WO 2010/078929 automated manufacturing is difficult and handling of the power source and LED lamp system during manufacturing requires a high degree of manual labour. Hence specifically trained personnel is needed to assemble the device which results in high costs per unit. These problems are solved by the use of a housing comprising two separable parts, which advantageously permit the power source and preferably also the LED lamp system to be inserted into the two parts after the moulding is completed, rather than moulding the housing about the electrical components.

Surprisingly, although more parts are required, the use of a two-part housing simplifies the manufacturing process since it is possible to create an automated system for inserting the power source and joining the two parts of the housing. The two housing parts are assembled around and then enclose the power source and LED lamp system. The reduction in the amount of manual labour required leads to significant advantages in relation to the cost per unit and the time taken to manufacture each unit, both of which are greatly reduced.

The method of manufacture of the device is hence also considered inventive in its own right. Therefore, in a second aspect the present invention provides a method of manufacturing an irradiation device for insertion into an orifice of the body to provide photodynamic therapy, the device comprising: a housing adapted to be fully inserted and secured in the orifice, the housing enclosing an LED lamp system and a power source for powering the LED lamp system; wherein the device is independently operational while located in the orifice; the method comprising: moulding a first housing part from a resilient material and moulding a second housing part from a resilient material, wherein the first housing part consists of a chamber for holding the power source and an opening into the chamber is provided through a resilient opening part, and the second housing part is for holding the LED lamp system, the first and second housing parts being separate mouldings and preferably being formed separately from the LED lamp system; and the method further comprising:

closing the chamber by joining the first housing part to the second housing part in order to form the housing of the device.

The first and second housing parts are separable in that they are formed as two separate parts. They may be made as completely separate mouldings, or it may be possible to use a single moulding for both parts and then cut the two apart after moulding is completed. The first and second housing parts may be permanently or semi-permanently joined together during the manufacturing process. Advantages of the above aspects arise from the use of two parts that are separated during manufacture and brought together to seal the housing about the LED lamp system and power source.

The resilient opening part advantageously allows for an electrical coupling to pass from the power source to the LED lamp system. The resilience of the opening enables the electrical coupling to be easily assembled with the first housing part of the device.

In a preferred embodiment the resilient opening can be deformed to insert and/or remove the power source into or from the first housing part. Thus, the resilience of the resilient opening part may be such that it can be stretched open to a sufficient degree to allow the power source to be pushed through. Once the power source is within the first part then it is securely held in place by the resilient opening part, which returns elastically to its original, unstretched, configuration. This approach means that the join between the first and second housing parts may be the only opening into the housing and hence allows for a well sealed, preferably fluid-tight and/or gas-tight device that can easily be sterilized.

Alternatively, instead of pushing the battery through the resilient opening part into the first housing part, the device may include a battery cap to provide an opening into the first housing part, for example a cap at an opposite end of the first housing part to the resilient opening part. The battery cap may have a bayonet, screw or clip fitting to hold it in place once the battery has been inserted. An advantage of this arrangement is that the physician who inserts the device can activate the device by inserting the battery. Also, disposal of the battery is easier since it can be taken out after the use of the device and disposed separately, for example to permit recycling. A battery cap would also allow re-use of the device which may not be a preferred option in the developed world but could be a viable option especially in third world countries. Since the vagina/cervix is not a sterile environment, then a device for treatment of the cervix may simply be disinfected and re-used without a real risk for contamination.

The resilient opening part preferably comprises a neck part for holding the power source within the chamber. The neck part may be arranged to enclose a part of the width of the power source when it is within the chamber. Hence, the neck part is preferably a resilient narrowing of the entrance to the chamber to a size less than the width of the power source to thereby hold the power source within the chamber. For example, the neck part may form one or more shoulders across the end of the chamber. In a preferred embodiment the neck part has a slot shaped opening with resilient material at either side of the length of the slot forming two shoulders across the end of the chamber. This shape allows for deformation of the neck part to occur to insert the power source and/or electrical coupling without the need for significant stretching of the resilient material. Advantageously, the shape of the neck part may also allow for bending of the first housing part at the neck, enabling the chamber to flex relative to the outer of the opening part and the second housing part. This can improve patient comfort and may, for example, allow for good fit for variations in the position of the cervix, e.g. posterior cervix. In preferred embodiments the slot of the neck part has an internal opening with a width of 8 mm or more, preferably about 10 mm or more.

The chamber should be of sufficient size to hold the power source, and this may be with or without stretching of the resilient material that forms the walls of the chamber. In a preferred embodiment the chamber is sized to fit tightly around the power source, for example chamber may have dimensions the same as or slightly smaller than the dimensions of the power source. This ensures that the power source is securely held by the elasticity of the resilient material during use of the device and minimises the risk of damage to the electrical connections occurring due to movement of the power source. In another embodiment, the chamber comprises a separate holder or cradle to hold the power source and optionally also required electrical connections or couplings for the power source.

The electrical coupling from the power source to the LED lamp system preferably passes through the neck part. For example there may be a wire or other electrical connector extending from the power source to electrical connections at the LED lamp system. Preferably the power source is electrically connected to the LED lamp system whilst the first and second part of the housing are separated from one another. This simplifies the manufacturing process. The opening part of the first housing part may be arranged to provide a cavity for holding the excess length of the electrical connector (for example a coil of wire) that may be required to allow for the preferred sequence of manufacturing steps.

The power source preferably comprises one or more batteries. Suitable batteries include lithium batteries or equivalent of sufficient capacity which may also be stored for up to 10 years. For example a ½ AA size $LiMnO_2$ battery may be used. The slow loss of charge and small size of lithium ion batteries makes them particularly suited for use as the power supply for the device.

In order to increase the safety of the device, it is preferable that the power source is sealed within the housing. By sealed it is meant that the housing is fluid tight in use to prevent fluids leaking into or out of the device. With the two part housing the seal can be attained by a tight join between the first and second housing parts. Optionally a sealing media may be used at the joint between the first and second housing parts, such as an adhesive, gel or semi-solid sealant. Alternatively, if the resilient material is silicone, non-cured silicone may be used to seal the joint between the first and second housing parts. Another way to achieve a tight join between the first and second housing parts is vulcanization. Such a tight join is preferred not only for fluid tightness, but also for gas tightness, i.e. it also allows the use of ethylene oxide for sterilization of the device.

Preferably the opening part on the first housing part has a coupling part to join to and form a seal with a complementary shaped coupling part on the second housing part, for example by plug and socket arrangement, by elastic and/or friction fit. Preferably alignment markers are present on each of the housing parts, e.g. on the outside of the opening part of the first housing part and the outside of the complementary shaped coupling part, which need to be aligned when the housing parts are joined together to ensure the correct position of one housing parts to each other. The material of the housing may be selected for its ability to form a secure seal when two parts made of the material are in engagement. One of the two coupling parts may be stretched to place it around the other of the two coupling parts, thereby using the elasticity of the resilient material to hold the two housing parts together. When the two coupling parts are joined this closes the chamber and forms the complete housing by connection of the first and second housing parts.

The resilient material used to mould the housing parts can be any resilient material commonly used in medical devices; for example rubber, latex, silicone or other natural, semi-synthetic or synthetic polymers or copolymers, preferably silicone. In a preferred embodiment a part or all of the resilient material of the second housing part which holds the LED lamp system is at least partially transparent. The use of a resilient material that is at least partially transparent enables the second housing part to allow for passage of light from the LED lamp system to a treatment area on the patient without the need for a further translucent or transparent component. In a preferred embodiment, the same resilient material is used to mould the first and second housing part, with the resilient material of the second housing part being at least partially transparent and with the resilient material of the first housing part being opaque. Preferably, silicone is used to mould the first and second housing part wherein the silicone which is used to mould the first housing part contains pigments which makes it opaque to the light emitted by the LED lamp system.

Since the second housing part holds the LED lamp system it is preferred for the light for the photodynamic treatment to exit via a treatment surface on the second housing part and to be directed to a treatment area on the patient and wherein the treatment surface preferably has a size and/or shape adapted for complementary fit with said treatment area. It is therefore particularly preferred for the second housing part to be moulded of a material that is at least partially transparent. Transparency in the current context should be understood to mean transparency in relation to the light emitted by the LED lamp system, or at least those wavelengths of the light that are required to excite the photosensitiser, i.e. to perform the photodynamic treatment of the patient.

It is particularly preferred for the LED lamp system to be formed separate from the moulding of the second housing part. Hence, preferably, the LED lamp system is not encased or attached to the second housing part during the moulding process. The LED lamp system may include one or more of the LEDs, connecting circuitry, a control mechanism and a substrate such as board of a printed circuit board, for example. It is advantageous for the LED lamp system to be provided separate from the moulding during manufacture since this makes the process more straightforward to automate.

In preferred embodiments the second housing part has one or more moulded cavity to fit elements of the LED lamp system. The LED lamp system may comprise a circuit on a substrate with LEDs and other circuit elements protruding from a circuit board. In this case the second housing part may have cavities for holding the circuit elements. By use of the one or more moulded cavity the LED lamp system can be securely fitted in a known orientation relative to the second housing thereby ensure that the device can be manufactured with consistent light output characteristics. Further, by use of one or more moulded cavity, especially one or more moulded cavity which results in a tight fit between the LEDs of the LED lamp system and said cavities, efficient heat dissipation is achieved. Where the second housing part includes a treatment surface, as described below, then the one or more moulded cavity preferably act(s) to direct light from the LED lamp system through the material of the second housing part to the treatment surface.

The one or more moulded cavity may be enclosed by a fastening lip for securing elements of the LED lamp system within the cavity. For example the fastening lip may be a lip extending inwardly about all or a part of the circumference of the one or more moulded cavity. Since the housing part is moulded from a resilient material then the fastening lip can be deformed resiliently to allow insertion of the LED lamp system. Preferably, the one or more moulded cavity and the fastening lip are arranged to guide the LED lamp system into the correct position when the LED lamp system is pushed into the one or more moulded cavity. This increases ease of manufacture.

As with the device of WO 2010/078929 the device of the current invention is adapted to be fully inserted and secured in the orifice and does not require connection to an external power supply or light source during operation. By "independently operable" it is meant that the device can provide illumination for PDT without concurrent connection to any external device. The device is hence fully self-contained and forms an enclosed unit including both the light source and the power supply required for photodynamic procedures.

As well as increasing the comfort and minimising disruption to the patient, another advantage of the present invention, in common with WO 2010/078929, is that PDT is preferably carried out at very low mean irradiance, i.e. average irradiance of all LEDs the LED lamp system is comprised of. Irradiance refers to the radiant power incident on a unit area (seen from the light source, in contrast to fluence rate which is seen from the object/area that is illuminated) and is measured in units of $W/cm^2$. PDT carried out with illumination with low mean irradiances (e.g. 10 $mW/cm^2$) requires that the illumination will have to occur over a relatively long time period, e.g. many hours, in order to achieve the desired light dose necessary to achieve a therapeutic effect, and hence is impossible in a clinical (hospital) situation. However, illumination using low irradiances is known to strongly reduce the patient discomfort (pain) during illumination, and, if precursors like ALA or derivatives of ALA are used, may also improve the PDT effect by allowing a continuous build-up of endogenous porphyrins (from said precursors) and to prevent oxygen depletion during illumination (S. Jacques et al., "PDT with ALA/PPIX is enhanced by prolonged light exposure putatively by targeting mitochondria", SPIE Proceedings Vol. 2972, "Optical Methods for Tumor Treatment and Detection", ed. T. Dougherty, San Jose, February 1997, and M. Seshadri et al., Clin Cancer Res 14(9), 2796-2805 (2008)). The device according to the invention provides, in use, preferably a mean irradiance below 50 $mW/cm^2$, for example mean irradiance in the range of 0.5 to 40 $mW/cm^2$, preferably below 30 $mW/cm^2$, more preferably in the range of 2 to 20 $mW/cm^2$ and most preferably in the range of 5 to 10 $mW/cm^2$, e.g. 5 to 6 $mW/cm^2$, 6 to 7 $mW/cm^2$ and most preferred 7 $mW/cm^2$ to 8 $mW/cm^2$.

The device is therefore not only more "patient friendly", it can also increase the efficacy of the treatment.

The shape of the housing can vary, but is generally designed so that it comfortably fits within the orifice and remains in place independent of the patient's physical activity. Where the orifice of interest is the female reproductive system, suitable shapes for the outer portion of the housing can for example be similar to the shapes of some contraceptive devices used to prevent pregnancy, such as FemCap® and other similar devices intended for blocking sperm from entering the uterus. For other orifices, other suitable shapes and structures can be utilised, for example based on shapes known for use as suppositories and/or pharmaceutical pessaries.

Although the present invention has been created with the treatment of human patients in mind, it is also possible for the device to be used in the treatment of other animals.

Therefore the shape of the housing will be dependent on the orifice where treatment is required and on the anatomical structure of the animal on which the device is intended for use.

The device can comprise a slim housing, which the walls of the orifice will envelope and hold in place. When the device is for vaginal use the housing may, for example, be similar in size and shape to a tampon. The outer surface of the housing may be textured to improve the grip of the device. A textured surface can also be of benefit in providing a surface for the delivery of drugs, e.g. PDT drugs, to the area of the body that requires treatment.

To ensure a comfortable and effective treatment for each patient, devices of different sizes and/or shapes may be made available. For example, in the case of treatment of the cervix devices of three size may be provided for (i) patients that have not been pregnant, (ii) patients that have had a pregnancy but not carried to term and (iii) patients who have given birth.

For some orifices, for example the rectum, a simple 'torpedo' shape for the housing will enable the device to be inserted and secured. However, for other applications additional features may be present in order to ensure that the device is securely held within the orifice during use. Hence, for use in the treatment of diseases, lesions and conditions of the cervix the housing preferably comprises a flexible outer portion that can adjust its shape to form a secure fit with the vaginal walls and enables the device to be used within many different shapes and sizes of vagina. The flexible outer portion also helps to decrease the risk of slipping or misalignment of the device over an extended treatment period, during which the patient may be physically active. A similar outer portion may be used for a device intended for insertion in other orifices, if required.

Preferably the flexible outer portion is formed on the second housing part. The flexible outer portion is advantageously formed from the resilient material. Alternatively an expandable material could be used such that, after insertion, the outer portion of the housing expands to firmly grip the walls of the orifice. The expansion could be initiated through body heat, exposure to fluid, removal from a delivery device/instrument etc.

Forming the flexible outer portion from a resilient material enables the shape of the flexible portion to be altered while also providing a biasing outwards force to hold the device in place. In order to achieve this effect the outer diameter of the outer portion is preferably sized so that it must be reduced in order to insert the device into the orifice. The outer portion will then provide an outwards force toward the walls of the orifice.

The flexible outer portion can be any shape which is capable of creating a secure fit with the walls of the orifice. For example, the flexible outer portion may be provided in the form of a number of discrete legs, ridges or other protrusions radially and/or longitudinally spaced about and extending outward from the housing. In other embodiments the flexible outer portion may form a continuous outer surface of the housing. This surface could either form the whole or a part of the exterior of the housing. For example the outer portion may be a disk or cup-shaped section found at either the front or rear of the device, or a covering which extends over the entire length of the housing.

In a preferred embodiment the flexible outer portion forms a continuous surface which tapers outwards towards the rear end of the device i.e. the end of the device which, in use, is closest to the entrance of the orifice. For example the outer portion can be approximately frustoconical in shape.

The flexible outer portion may have a different configuration when in use to the configuration when formed during moulding. This can make the moulding process simpler by simplifying the shape of the moulding. It also allows for the flexible outer portion to have change configuration when it is inserted or removed from the body orifice, which can be more comfortable for the patient. In a preferred embodiment of this type the second housing part is moulded with a flexible outer portion having a continuous surface as described above that, in the as-moulded configuration tapers outward toward the front end of the device, and which is arranged to fold elastically into a second stable configuration where the flexible outer portion is reverse and folds back on itself so that it tapers outward toward the rear end of the device. This allows the flexible outer portion to be fitted securely into the orifice during use, and also allows removal from the orifice to be more comfortable for the patient since the flexible outer portion can return to its as-moulded configuration as the device is removed.

For insertion into the ear or nose the device may be shaped based on known designs for ear or nose plugs.

Preferably the housing comprises a treatment surface, the LED lamp system being arranged to emit light from the treatment surface. The treatment surface is preferably on the second housing part. The device can be arranged to provide irradiation to the walls of the orifice, in which case the treatment surface may be an outer circumferential surface of the housing. The treatment surface preferably has a size and or shape selected for complementary fit with the treatment area, and is preferably sized to confront the entire area where PDT is required. The LED lamp system and treatment surface are preferably arranged such that light is emitted toward the treatment area at sufficient proximity to achieve the desired treatment effect.

The device may be arranged to provide irradiation to a particular area of the inside of the orifice. Thus, the treatment surface may be arranged to direct and/or focus light onto a particular treatment area of the inside of the orifice when the device is in use. In one preferred embodiment the device is adapted for use in PDT of the cervix, i.e. the cervix is the treatment area of interest. Therefore, the treatment surface is preferably shaped so as to cover, in use, the external opening of the cervix. When the device is correctly inserted into the vagina the treatment surface will cover the opening of the cervix and hence enable the emitted light to irradiate the cervical area.

The size of this treatment surface should be such that it fits over the entire portion of the cervix, for example it may be 20-50 mm in diameter, more preferably 20-35 mm in diameter and most preferably 22-30 mm in diameter.

In some embodiments the treatment surface may be fully transparent to light having the wavelengths required for PDT treatment and being emitted by the LED lamp system. Preferably, the treatment surface is at least partially transparent. However, preferably the material of the treatment surface and/or other material between the treatment surface and the light emitting portion(s) of the LED lamp system is arranged to diffuse the light, thereby enabling an even distribution of light from the LEDs. In one embodiment, a transparent material is used to form the second housing part such that the treatment surface is fully transparent. In an alternative embodiment, a transparent material is used to form the treatment surface while a non (fully) transparent material is used to form the second housing part. This will ensure that only the area in need of treatment is illuminated while other areas which get in contact with the device are not subjected to irradiation. However, in a preferred embodiment, the second housing is made from a single material which is at least partially transparent. Preferably, an at least partially transparent silicone is used as a material for the second housing part.

In other embodiments the LED lamp system may be positioned on or extend out of the treatment surface. In such embodiments it is not necessary for the light to pass through the treatment surface and hence no constraints are placed on its opacity. However, in a preferred embodiment the LED lamp system is positioned below the treatment surface.

In one preferred embodiment the treatment surface is concave. This can assist in directing the emitted light towards a convex treatment area, such as the cervix.

In embodiments designed for providing irradiation to the cervix, the device may comprise a protrusion that extends outwardly of the device from the treatment surface. Preferably this protrusion forms a cylindrical tube. This can be used both to assist in the correct positioning of the device within the vagina and also to direct light to the cervical canal. In the latter case the tube acts as a light tube.

Preferably the flexible outer portion is located to the rear of the treatment surface. This prevents any interference with the light treatment. In preferred embodiments in which the outer portion is a continuous surface the outer portion can extend from the treatment surface towards to rear of the device, tapering outwards such that the widest section of the outer portion is, in use, located rearwards of the treatment surface.

The LED lamp system may comprise one LED or preferably an array of LEDs. A particularly preferred LED array for PCT of cervix comprises 3-15 LEDs, more preferably 7 LEDs. The term "LED" is intended to cover any form of light emitting diode, for example OLEDs (organic light emitting diode), quantum dot LEDs or LECs (light emitting electrochemical cells, as described in A. Sandström et al., Nat. Commun. 3, 2012, 1002).

The energy consumption per unit time of the LED lamp system should be such that the heating of tissue of the treatment area does not result in undue discomfort or damage to the patient. The light will in general be applied at a dose of 10-200 $J/cm^2$, for example at 20 to 150 $J/cm^2$, preferably 30 to 140 $J/cm^2$, optionally 30 to 100 $J/cm^2$, and more preferably 100 to 130 $J/cm^2$, e.g. 37 $J/cm^2$ or 40 $J/cm^2$ or 125 $J/cm^2$, and this light dose is preferably provided at a low mean irradiance over several hours, as discussed earlier. In a preferred embodiment, the device according to the invention when used for providing PDT to the cervix, provides light at a mean irradiance of about 6-8 $mW/cm^2$, preferably of a about 7 $mW/cm^2$ over a period of 4 to 6 hours, preferably 4 to 5 hours thus delivering a light dose of about 85 to 175 $J/cm^2$. The wavelength of light used for the PDT is selected to excite the photosensitiser and hence the LEDs are selected for their ability to emit wavelengths of light suitable for this effect. In one preferred embodiment the LEDs emit, in use, light having wavelengths in the range of 300-800 nm, for example, the range 500-700 nm has been found to be particularly effective. It can be particularly important to include the wavelengths 630 and 690 nm or 632 and 690 nm. Therefore, preferably the at least one LED emits, in use, light having wavelengths in the range of 630-690 nm, most preferably light having a wavelength of 635±5 nm. In a most preferred embodiment, especially if the device is used together with a composition comprising a photosensitiser precursor selected from 5-aminolevulinic acid or a derivative, e.g. an ester thereof, red light (600-670 nm) is used since light at this wavelength is known to penetrate well into tissue. In some embodiments the LED lamp system comprises filters to ensure that only light within a certain wavelength range, such as those mentioned above, is emitted from the device. The treatment surface may be designed such that only light having these preferred wavelengths is transmitted.

At its most basic the LED lamp system may simply comprise electrical connections for the power supply and one or more LEDs. With this arrangement, immediately prior to insertion of the device the lamp system would be activated to switch on the one or more LEDs. The device would then be inserted into the orifice where the LED(s) will illuminate the treatment area until the device is removed, the power supply is depleted or the pre-programmed illumination time has elapsed.

Activation of the LED lamp system may be triggered by a switch. In order to allow the device to be maintained sterile or clean and to keep the power source and other elements of the device enclosed, the switch is preferably enclosed within the housing when the two housing parts are joined and arranged to be operated whilst sealed within the housing. The switch may be a mechanical switch located beneath e.g. a flexible part of the housing, with operation of the switch being permitted by the resilience of the flexible part. Alternatively the switch may be operated by means of an electrical or magnetic field transmitted through the housing. A magnetically operated switch may be implemented by the use of a magnet outside the housing, preferably a magnet which is part of the packaging of the device, to hold a 'normally closed' reed switch, preferably a read switch comprised in a holder or cradle for the power source, open. When the magnet is removed, e.g. the device is taken out of its packaging, the reed switch will close and this can be used to activate the device.

In a simple system using just a power source and a LED lamp system it is hard to control the light dose which is delivered when the device is in use, as the precise life and power output of the power source will vary. In addition the light provided by the LED lamp system will be constant. In order to avoid unacceptable heating of tissue of the treatment area, light at low irradiance is preferably used. It may also be beneficial for the device to be able to provide pulsed light.

Therefore preferably the LED lamp system further comprises a control circuit, such as a microcontroller or microprocessor, for regulating the light provided by the at least one LED. The control circuit of the LED lamp system may be activated by a switch as described above. In a preferred embodiment the control circuit comprises a timer. The LED lamp system can then be programmed to begin illumination at a pre-determined time interval after activation. This ensures that sufficient time has passed from activation to the start of illumination. For example, in order to allow the uptake of a photosensitiser or precursor into the target cells or build up of the photosensitser from a precursor/conversion of a precursor into a photosensitiser (e.g. the build up of porphyrins from a 5-ALA precursor or a 5-ALA derivative precursor) a certain time is required after application/administration of a photosensitiser or precursor. The length of illumination can also be strictly controlled as the control circuit can be arranged to switch off illumination after a pre-determined time has elapsed and hence a certain light dose has been provided. To allow further intracellular build-up of photosensitisers from precursors after the first illumination, the device may repeat the illumination (re-PDT) after a certain period of time, e.g. 3 hours.

In addition the control circuit may be arranged to provide pulsed illumination. This can be achieved by providing a function generator within a microprocessor. As mentioned above, pulsed light is advantageous in ensuring that no unacceptable heating of tissue occurs. In addition, providing intervals in illumination enhances tissue oxygenation and the effect of PDT. Further it allows for the re-accumulation of intracellular photosensitisers from precursors in surviving cells that can be treated with repeated illuminations. The frequency and length of the pulses can be chosen according to the requirements of the treatment regime and set within the control circuit.

In one embodiment, the control circuit can be programmed by the user. This enables the length, strength and illumination pattern to be adjusted to suit individual treatments.

Suitable re-writable memory forms include EPROM, EEPROM, flash etc. However, the control circuit memory is preferably read only (ROM) and programmed at the time of manufacture.

Access to the control circuit could be achieved by means of a user interface on the device. By answering a series of questions the user can set the initial delay period, dosage duration, number and length of light pulses etc. The interface may be integral with the device. Thus, it may comprise small buttons that may be pressed with a suitable tool or reed switches. Each button or switch may activate a given pre-set condition such as light dose, intensity, pulsed/steady light, etc.

It is important that all the electrical components of the LED lamp system and power source are sealed within the housing during use. Therefore the control circuit should preferably be sealed within the housing. As mentioned previously the LED(s) could be positioned such that these protrude from the housing. However, preferably the LED lamp system is entirely sealed within the housing during use.

In some embodiments the user interface may be accessible through e.g. a flexible area of the housing. Alternatively the housing may comprise a sealable opening which provides access to the interface.

The provision of a user interface however increases the size of the LED lamp system and/or the device, which may be undesirable in certain applications. Therefore, alternatively, the control circuit may comprise a receiver for connection to a remote terminal. In this way specific program commands can be communicated from the remote terminal, e.g. a computer, to the control circuit.

The receiver may comprise an input port adapted for connection to a cable. In such embodiments the input port is suitably shaped to receive, for example, a USB or other male connector.

The input port must be sealed during use. Therefore the housing may comprise a plug for insertion into the port. Alternatively the program commands may be transmitted to the device by means of a wireless connection. For example, the receiver may be an infra-red or radio wave receiver or bluetooth. This has the advantage that a physical input port is not necessary and instead the control circuit can be permanently sealed within the housing.

Preferably the control circuit further comprises a feedback system. This enables the control circuit to make adjustments in the treatment program to account for deviations in expected LED performance.

For example, the feedback system may comprise a light monitor or other direct or indirect monitor to measure the light dose that has been given to the patient. In such systems the control circuit may be programmed to switch off the LED(s) after a pre-determined light dose has been delivered rather than a pre-determined time.

Alternatively a dosimeter may override the timer in the event that the LEDs do not operate as expected. For example, if the power supply is faulty the output of the LEDs may be reduced. Therefore it will be necessary to continue illumination beyond the pre-determined time in order to provide the complete light dose. Conversely if the power output of the LEDs is stronger than anticipated the illumination can be stopped ahead of the pre-determined time interval, or the duration of each pulse can be shortened to prevent overheating of tissue.

The control circuit may further comprise a temperature sensor which allows illumination with high irradiances, e.g. irradiances above 50 mW/cm2, until the target tissue reaches a certain temperature, e.g. 40-43° C. When said temperature is reached, the illumination stops until the temperature of the target tissue decreases, e.g. to 37-38° C. At this temperature, illumination is switched on again.

The control circuit may further comprise a proximity sensor which measures the distance between the treatment surface and the treatment area on the patient and thereby detects misplacement or misfits. In such instances, the illumination is either paused or the device is not activated at all. An appropriate feedback is given to the user. A proximity sensor can also work as an on/off switch for the device.

Another optional feature of the control circuit is one or more performance indicator lights for informing a user whether the device has operated correctly or whether a fault has occurred. The control circuit may be arranged to provide a signal to the user when treatment is complete to indicate that the device can be removed. For example an acoustic and/or visual signal may be provided, such as an alarm sound and/or a light signal. Alternatively or in addition, a vibration could be used as the signal to indicate the end of the treatment. Typically the patient would be informed of the length of the treatment and so the signal can be used to confirm an expected end of the treatment and hence need not be overly intrusive. Alternatively, the user can use an app, e.g. on his/her mobile phone, tablet or computer to get the aforementioned information.

Advantageously, as the control circuit may be used to turn off the LEDs at the end of the treatment there is no great ill effect for the patient if the device remains inserted for longer than the treatment time. However, it is expected that patients will wish to know when treatment has ended and the device can be removed.

Preferably some or all of the above mentioned features of the control circuit are contained in a microprocessor.

The device may comprise a lens system arranged to provide homogenous illumination over the treatment area. The treatment surface and/or material of the housing adjacent thereto may act as the lens system. For example, this surface may be formed of silicone or another material comprising surface elements for diffusing the light emitted by the LED(s).

In use the device is preferably placed into the orifice by a doctor, a nurse or another person with experience or education within relevant fields. However, patients might in some situations choose to insert the device themselves.

In one preferred embodiment the device comprises a handle at its rear end. The handle can be used by the patient or medical practitioner to firmly grip the device during insertion and removal. The chamber for the power source may additionally act as the handle for the device.

However, preferably the device comprises an attachment point for a removal cord, for example a hole or eye. A removal cord may be attached to the device for use in pulling the device out of the orifice.

Another option is for the device to be placed (and removed) using a specific instrument, such as a pair of tweezers.

Advantageously, the device is designed for a single-use and for disposal after that single use. Preferably, the device includes one or more features that promote single-use and/or prevent repeat use. For example, the power source may be arranged to provide power that is only sufficient for a single-use, i.e. such that the power source is depleted after the required treatment is complete. The power source may be arranged so as not to be re-charged, and/or the control circuit may lack access to re-charge the power source. The control circuit may be arranged to prevent re-use by means of features of its programming and/or it may include a deactivation mechanism that destroys circuitry or software when triggered. To prevent patient interference when in use, the control circuit may also be arranged to selectively deactivate if interference is detected. By enforcing single use patient safety is improved and a strict control of sterility of the device is ensured.

The device can be used to provide PDT according to the following method. A composition comprising a photosensitiser or precursor thereof (hereinafter "composition") is applied to the area to be treated or the area of interest is treated by means of a systematically acting composition. Such a systematically acting composition may be supplied intravenously or orally, for example. The composition may be applied by a physician, where applicable by using a specialised applicator, or alternatively it may be applied by means of a drug delivery system on the device, for example as discussed below. The device is activated and inserted. The patients can then immediately leave the medical facility and continue their normal daily routine while the treatment area is receiving illumination from the device. In this way treatment can occur over a prolonged period of time without inconvenience to the patient. After the treatment is complete the patients can either return to the medical institution for removal of the device or remove it themselves. The device can either be discarded or returned to the medical institution for disposal.

In a preferred embodiment the device of the present invention further comprises a drug delivery system. The drug delivery system may comprise a drug carrying area on the housing, preferably a drug carrying area on a treatment surface. This might be a textured surface for carrying a composition of photosensitiser or precursor or the treatment surface itself without any further modifications may act as the drug carrying area. Alternatively, the drug delivery system may comprise a reservoir for housing a composition comprising a photosensitiser or precursor thereof (hereinafter "composition").

A significant advantage of this is that the patient need not wait at the hospital for several hours between application of the composition and illumination, as is normal in existing PDT procedures. The device may automatically perform the illumination either immediately upon application or preferably at a later time. In addition, only one invasive procedure is required.

Optionally the drug delivery system further comprises a physical, mechanical or electrical system related to delivery. Such an optional system may include, for example, filters, membranes, one or more reservoirs arranged to deliver the composition based upon a preset plan or based on physical conditions, such as for example pH, osmolality, temperature, pressure, water content in the surroundings. However, the simplest and in most cases the most preferred drug delivery system is just a single drug carrying area for carrying the composition, and in a most preferred embodiment, the drug carrying area is the treatment surface itself.

In this preferred embodiment the method of use is similar to that described above except that the composition is not applied to the treatment area in a separate procedure. Instead the composition is applied to the drug carrying area, e.g. the treatment surface, and is hence applied to the treatment area on the body of the patient upon insertion of the device into the orifice. Illumination is then conducted as described above.

The composition can be supplied together with the device (i.e. a pre-filled device), preferably in such a way as described in WO 2012/004399. In such instances the drug delivery system, i.e. drug carrying area or reservoir, preferably treatment surface, may be supplied with a cover, such as a foil or cap, to seal the composition within the device until use. Prior to insertion the cover is removed so that the composition can be released. Alternatively the device can be supplied separately from the composition. This enables the physician to choose the optimal composition for a particular case and add this to the drug delivery system, i.e. drug carrying area or reservoir, preferably treatment surface, prior to insertion.

The composition to be used with the device, whether in a pre-filled device or applied to the device before use or applied to the treatment area separately, may comprise any suitable photosensitiser or precursor of a photosensitiser.

A range of photosensitisers are known in the art. As discussed above, one type of such compounds are compounds that per se are phototoxic to target cells or species or have light emitting properties when exposed to light. Such compounds have relatively large molecular weights and are often complex molecules. Typical photosensitisers include dyes like hypericin and PVP hypericin, psoralens, porphyrins such as hematoporphyrins, protoporphyrins, uroporphyrins, coproporphyrins, benzoporphyrins or deuteroporphyrins, in particular Photofrin® (profimer sodium), photosan III or verteporfin; chlorins, including bacteriochlorins and isochlorins such as chlorine e6, talaporfin or temoporfin and phthalocyanines such as aluminium- and silicon phthalocyanines.

Another type of photosensitisers are compounds that not per se are toxic or light emitting, but form photosensitisers in vivo. Such compounds—referred to herein as precursors—are typically 5-aminolevulinic acid (5-ALA) and derivatives of 5-ALA, like 5-ALA esters. A composition comprising either type of compound can be used or supplied with the present device.

5-aminolevulinic acid (5-ALA) and its derivatives are amongst the most clinically useful precursors known in the art. These compounds are converted in the body to protoporphyrin IX (PpIX), which is a photosensitiser that absorbs light and in contact with oxygen generates singlet oxygen. Singlet oxygen is extremely reactive and reacts fast with various cellular biomolecules resulting in cell death.

5-ALA and its derivatives are widely known and used in methods of photodynamic therapy (PDT) for the treatment of various abnormalities or disorders of the skin or other epithelial organs or mucosa, especially cancers or pre-cancerous lesions, as well as certain non-malignant lesions, e.g. skin diseases such as actinic keratosis (AK) and acne. 5-ALA (Levulan®, Dusa) and 5-ALA methyl ester (Metvix®, Galderma, Switzerland) are commercial products for PDT of actinic keratosis and basal cell carcinoma.

The use of 5-ALA and derivatives thereof, e.g. 5-ALA esters in PDT is well known in the scientific and patent literature (see, for example, WO 2005/092838, WO 02/09690, WO 02/10120 and WO 96/28412) and all such compounds and their pharmaceutically acceptable salts are suitable for use with the device herein described.

Esters of 5-aminolevulinic acid and their pharmaceutically acceptable salts are preferred precursors in a composition for use with the invention, see, for example, WO 96/28412 and WO 02/10120 to Photocure ASA.

Preferred examples of such precursors include those of formula (I) and pharmaceutically acceptable salts thereof:

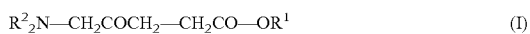

wherein
$R^1$ represents a substituted or unsubstituted alkyl group; and
$R^2$ each independently represents a hydrogen atom or a group $R^1$.

Such precursors and their synthesis have been described in WO 2005/092838, WO 02/09690, WO 02/10120 and WO 96/28412.

As used herein, the term "alkyl", unless stated otherwise, includes any long or short chain, cyclic, straight-chained or branched saturated or unsaturated aliphatic hydrocarbon group. The unsaturated alkyl groups may be mono- or polyunsaturated and include both alkenyl and alkynyl groups. Unless stated otherwise, such alkyl groups may contain up to 40 carbon atoms. However, alkyl groups containing up to 30 carbon atoms, preferably up to 10, particularly preferably up to 8, especially preferably up to 6 carbon atoms are preferred.

In compounds of formula I, the $R^1$ groups are substituted or unsubstituted alkyl groups. If $R^1$ is a substituted alkyl group, one or more substituents are either attached to the alkyl group and/or interrupt the alkyl group. Suitable substituents that are attached to the alkyl group are those selected from: hydroxy, alkoxy, acyloxy, alkoxycarbonyloxy, amino, aryl, nitro, oxo, fluoro, —$SR_3$, —$NR^3_2$ and —$PR^3_2$, wherein $R^3$ is a hydrogen atom or a $C_{1-6}$ alkyl group. Suitable substituents that interrupted the alkyl group are those selected from: —O—, —$NR_3$—, —S— or —$PR_3$.

If $R^1$ is a substituted alkyl group, one or more aryl substituents, i.e. aryl groups, preferably one aryl group, are preferred.

As used herein, the term "aryl group" denotes an aromatic group which may or may not contain heteroatoms like nitrogen, oxygen or sulphur. Aryl groups which do not contain heteroatoms are preferred. Preferred aryl groups comprise up to 20 carbon atoms, more preferably up to 12 carbon atoms, for example, 10 or 6 carbon atoms. Preferred embodiments of aryl groups are phenyl and naphthyl, especially phenyl. Further, the aryl group may optionally be substituted by one or more, more preferably one or two, substituents. Preferably, the aryl group is substituted at the meta or para position, most preferably the para position. Suitable substituents include halo alkyl, e.g. trifluoromethyl, alkoxy, preferably alkoxy groups containing 1 to 6 carbon atoms, halo, e.g. iodo, bromo, chloro or fluoro, preferably chloro and fluoro, nitro and $C_{1-6}$ alkyl, preferably $C_{1-4}$ alkyl. Preferred $C_{1-6}$ alkyl groups include methyl, isopropyl and t-butyl, particularly methyl. Particularly preferred aryl substituents are chloro and nitro. However, still more preferably the aryl group is unsubstituted.

If $R^1$ is an unsubstituted alkyl group, $R^1$ groups that are saturated straight-chained or branched alkyl groups are preferred. If $R^1$ is a saturated straight-chained alkyl group, $C_{1-10}$ straight-chained alkyl group are preferred. Representative examples of suitable straight-chained alkyl groups include methyl, ethyl, n-propyl, n-butyl, n-pentyl, n-hexyl and n-octyl. Particularly preferred are $C_{1-6}$ straight-chained alkyl group, most particularly preferred methyl and n-hexyl. If $R^1$ is a saturated branched alkyl group, such branched alkyl groups preferably consists of a stem of 4 to 8, preferably 5 to 8 straight-chained carbon atoms which is branched by one or more $C_{1-6}$ alkyl groups, preferably $C_{1-2}$ alkyl groups.

In compounds of formula I, each $R^2$ independently represents a hydrogen atom or a group $R^1$. Particularly preferred for use in the invention are those compounds of formula I in which at least one $R^2$ represents a hydrogen atom. In especially preferred compounds each $R^2$ represents a hydrogen atom.

The most preferred precursors to be used in a composition together with the devices according to the invention are compounds of formula I and pharmaceutically acceptable salts thereof, wherein $R^1$ is $C_1$-$C_6$ alkyl, e.g. hexyl, more preferably straight chain $C_1$-$C_6$ alkyl, e.g. n-hexyl and both $R^2$ represent hydrogen, i.e. 5-ALA hexyl ester and pharmaceutically acceptable salts thereof, preferably the HCl salts. The most preferred precursor is 5-ALA hexyl ester and the most preferred pharmaceutically acceptable salt of 5-ALA hexyl ester is the HCl salt.

The composition comprising the photosensitiser or precursor to be used together with the device of the invention can be any type of pharmaceutical formulation and may be prepared by any conventional procedure available in the art. Preferred compositions comprising systemically acting photosensitisers or precursors for oral or intravenous administration are liquids (aqueous and non-aqueous) or solids such as, tablets or pills. Preferred compositions comprising photosensitisers or precursors for local application are liquids (aqueous and non-aqueous), semi-solids such as lotions, creams, ointments, gels or pastes, foams or other expandable compositions (for example based on heating to body-temperature) and compositions comprised in patches. Semi-solid compositions such as described in WO 2010/142457 are preferred. Most preferred are semi-solid compositions, e.g. ointments comprising a precursor, preferably a precursor of formula (I). The components in the composition are the same components found in pharmaceutical products on the market, and a listing of such components can be found in handbooks of pharmaceutical excipients.

It is important for locally applied formulations that the formulation is as such that the composition is well absorbed into the tissue of the treatment area or that it is transparent in order not to interfere with the illumination.

Viewed from another aspect the present invention provides a method of photodynamic therapy of a treatment area within an orifice of the body, the method comprising: applying a composition comprising a photosensitiser or precursor to the treatment area and using the device according to the invention or preferred embodiments thereof, as described above, to treat the treatment area. As such, the LED lamp system of the device operates to provide illumination to the treatment area.

The method may include a step of selecting a device of suitable size and/or shape. The device may be selected firstly to suit the orifice concerned, and secondly to suit different patient conditions. For example, a device for treatment of the cervix would preferably be selected from a range of sizes depending on the patient's history of pregnancy.

The composition may be applied to the treatment area prior to insertion of the device, and this may be done by directly applying the composition, where applicable by using a suitable applicator. Alternatively, the composition may be applied systemically, if it contains a systemically acting photosensitiser or precursor. In an alternative preferred embodiment the composition is supplied via a drug delivery system of the device such that the steps of application of the composition and insertion of the device occur simultaneously. The drug delivery system may comprise a drug carrying area or reservoir or may simply be the treatment surface of the device, as discussed above.

The light will in general provided by the device at such mean irradiance over such periods and at such wavelengths as discussed above to deliver light doses as discussed above.

The device can be provided separately from the composition or with the composition already contained within a drug delivery system. Alternatively the device can be provided in the form of a kit comprising the device and at least one separate composition for use with the device, preferably a semi-solid composition comprising a photosensitiser or precursor which is provided in a suitable container, e.g. a tube or jar.

The device can be used for providing PDT to a body orifice. Preferably, the device is used for the photodynamic treatment of conditions, lesions, abnormalities and diseases of the female reproductive system, preferably the vagina and cervix. More preferably the device is used for the photodynamic treatment of HPV infections, intraepithelial neoplasia, dysplasia, precancerous lesions and cancer of the female reproductive system, preferably the vagina and cervix.

The present device and method for photodynamic treatment may be combined with other therapeutic procedures, for example administration of other therapeutic drugs. These therapeutic drugs might be administered into the body prior to or together with placing the device in the orifice or might be administered through other routes of administration (e.g. oral, intravascular or dermal). Typically such drugs include hormones, antibacterial agents, antifungal agents, antiviral agents, anticancer agents or combination of such drugs.

Although some of the preferred features of the invention have been described in relation to providing PDT to the vagina and cervix, it will be appreciated that these features device could advantageously be included in devices for use in other body orifices, such as devices for the rectum, ear or nose, as discussed above. The present invention is not limited as to the particular orifice that it is to be used in, but instead the invention provides a device and method that can be beneficially used in the treatment of various conditions in different orifices.

Certain preferred embodiments of the present invention will now be described, by way of example only, with reference to the accompanying drawings in which.

Figure 1:
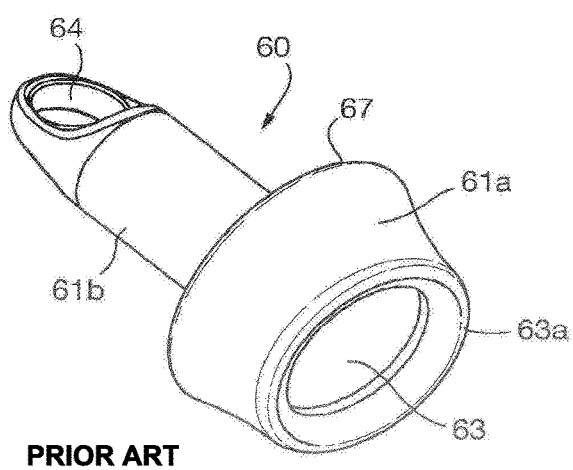
FIGS. 1 to 4 show a perspective view, side elevation, end elevation and cross-section view of a prior art irradiation device disclosed in WO 2010/078929.
Figure 2:
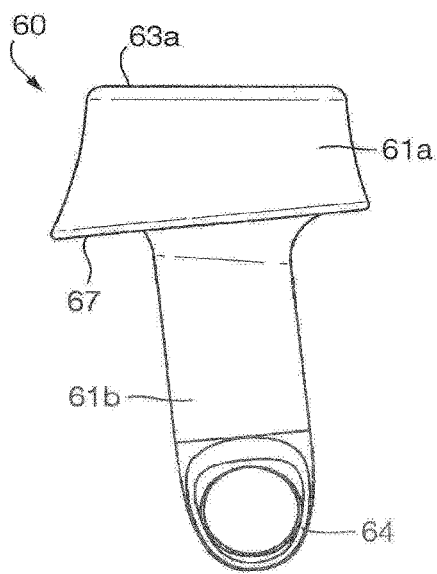
Figure 3:
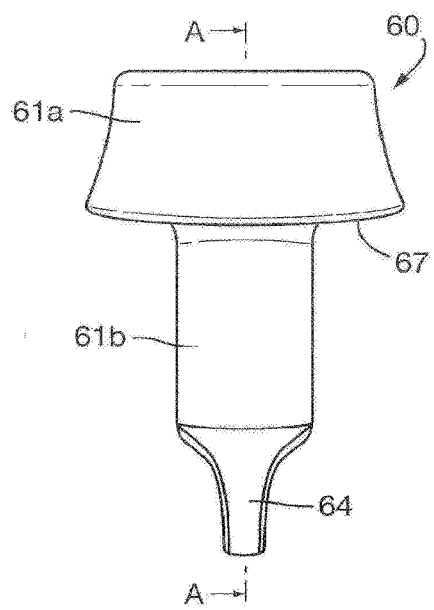
Figure 4:
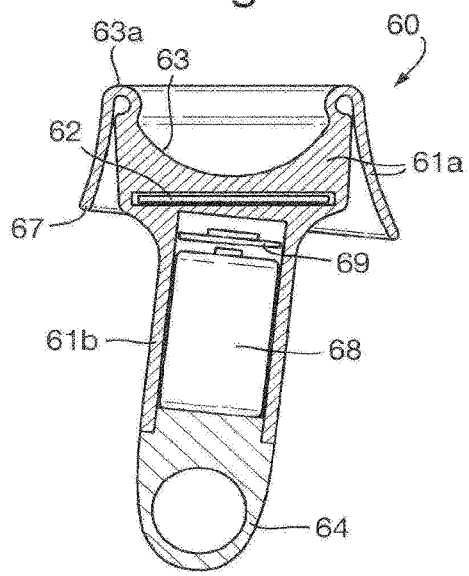
Figure 5:
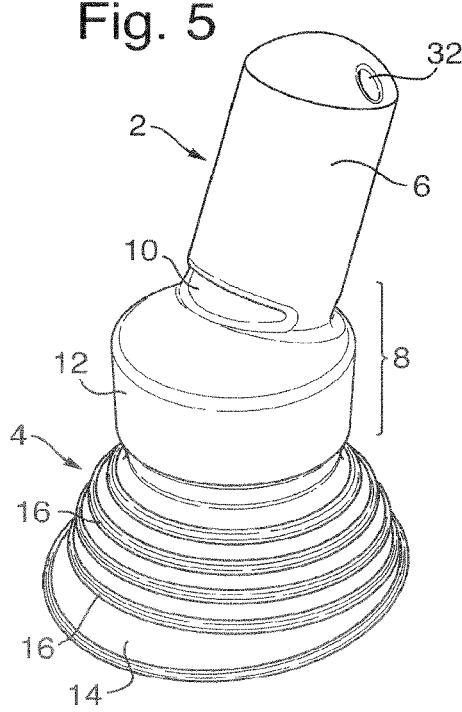
FIG. 5 shows an embodiment of a device with a two-part housing in perspective view
Figure 6:
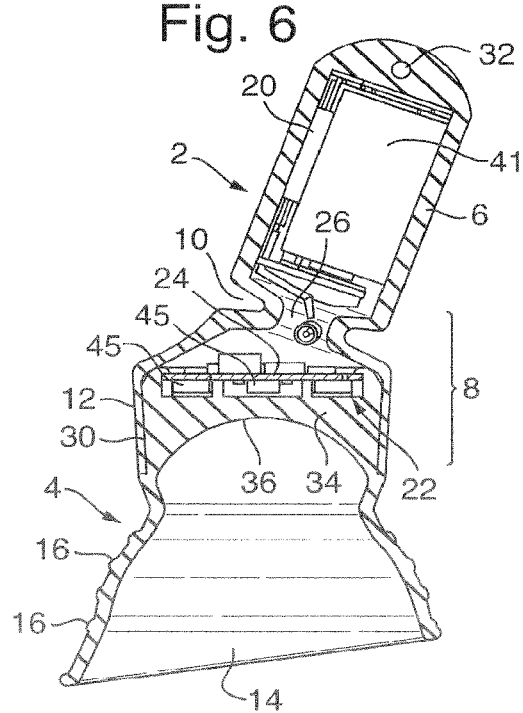
FIG. 6 is a cross-section elevation through the device of FIG. 5
Figure 10:
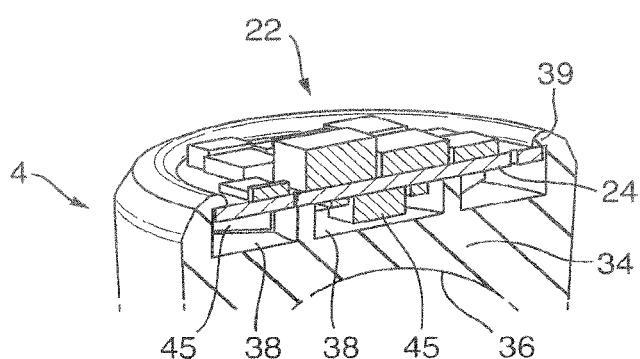
FIG. 10 is a close up cut-away perspective view of the second housing part with an LED lamp system installed thereon.
Figure 11:
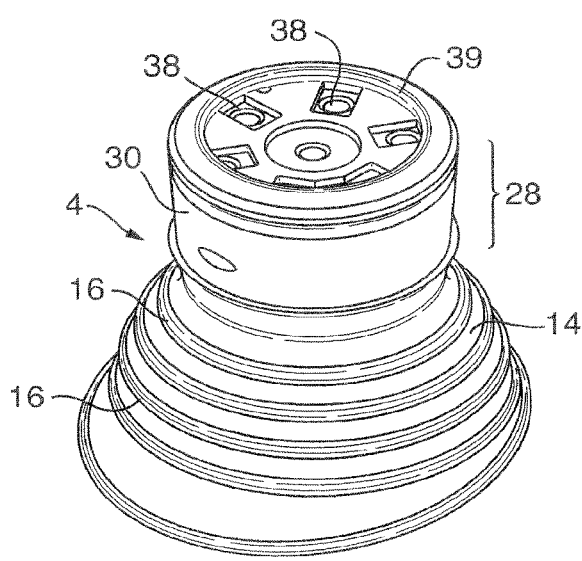
FIG. 11 is a perspective view of an alternative preferred embodiment for the second housing part.
Figure 12:
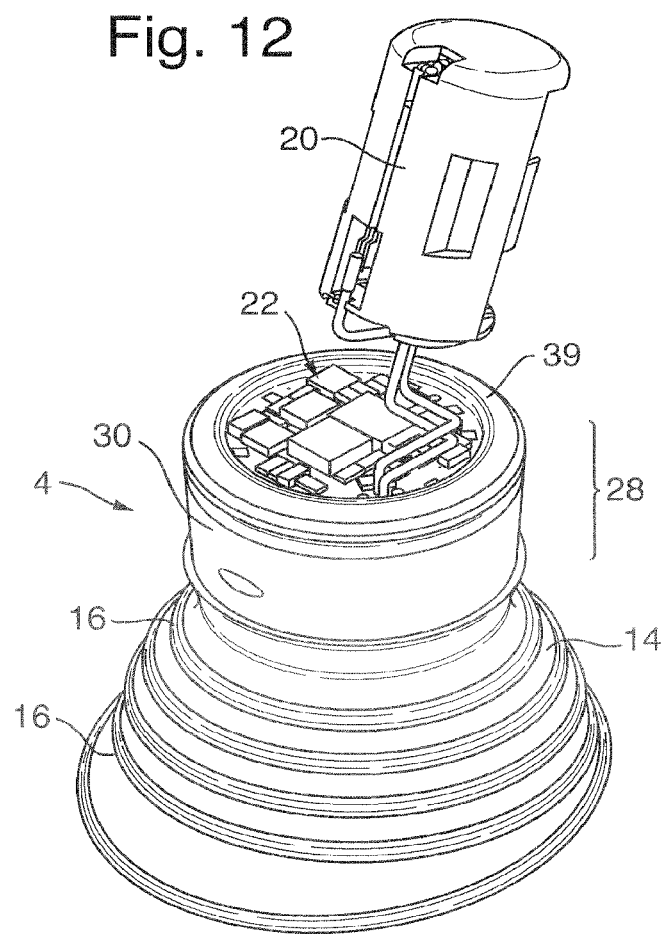
FIG. 12 shows the second housing part of FIG. 11 along with the LED lamp system and power source holder, i.e. battery holder.
Figure 14A:
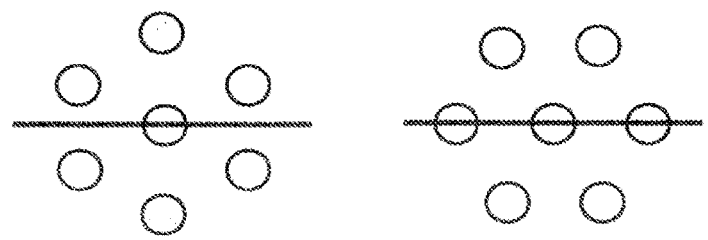
Figure 14B:
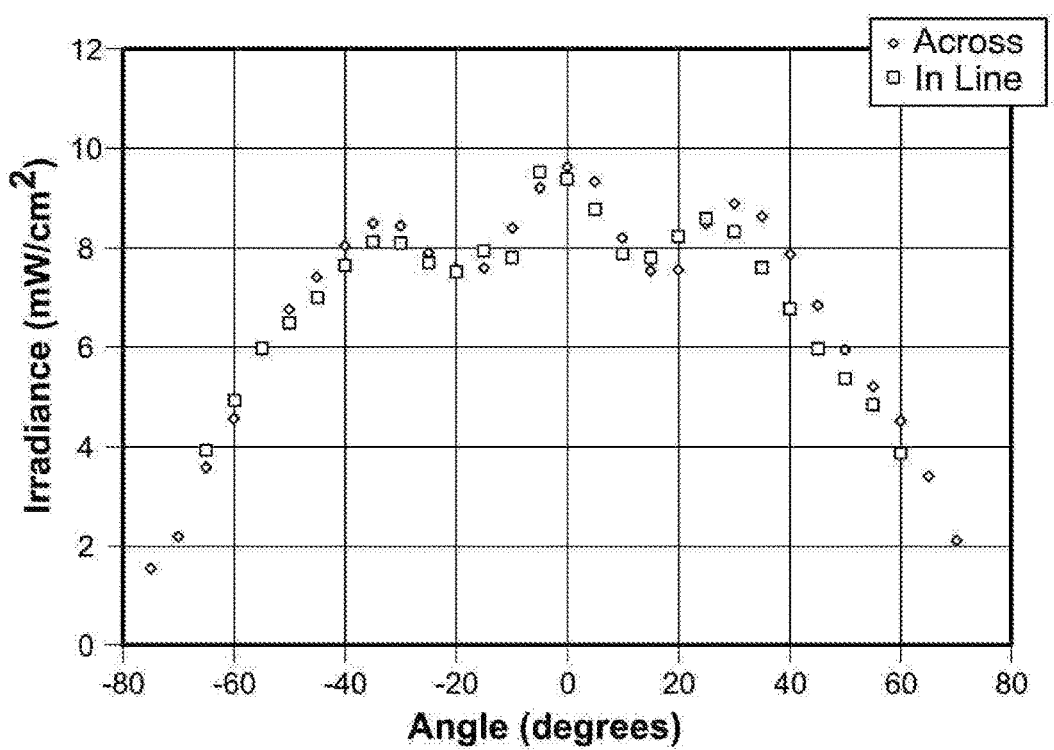

FIG. 14a shows the orientation of the LEDs of the LED lamp system of a device according to FIGS. 5-12 during irradiance measurement FIG. 14b shows the measured irradiance profile of a device according to FIGS. 6 and 12 across a concave treatment surface The prior art device of FIGS. 1 to 4 is an irradiation device 60 for photodynamic therapy of the cervix. FIGS. 1 to 3 show perspective, side and end views. FIG. 4 is a cross-section along line A-A on FIG. 3. The device 60 is arranged for use in photodynamic treatment of the cervix and has a single part housing 61 including an upper housing portion 61a and a lower cylindrical housing portion 61b extending beneath the upper housing portion. The upper housing portion 61a is flexible and includes an outer portion 67 that is approximately frustoconical in shape and tapers outwards from the front end of the device 60 to the rear. The outer portion 67 is resilient such that, in use, this presses against the walls of the vagina in order to securely hold the device 60 in place. The shape of the upper housing portion 61a and its outer portion 67 can most clearly be seen in FIG. 4.

An LED lamp system 62 is sealed within the upper housing 61a. The power supply for the lamp system is a battery 68 enclosed within the cylindrical housing portion 61b. The battery is a ½ AA size battery with the cylindrical housing portion 61b formed relatively tightly around it. The control circuit 69 is also enclosed with the battery, and advantageously this takes the form of a PCB with a diameter the same as the battery diameter, for efficient use of space.

The front end of the upper housing 61a forms a treatment surface 63, which is a lens of transparent material covering the LEDs of the LED lamp system 62. This material is a transparent silicone which also forms the remainder of the flexible housing of the device 60. An opaque white silicone over-moulding is used to cover the sides of the upper housing portion 61a, both about the outer portion 67 and also on the sides within the outer portion 67, and to completely cover the cylindrical portion 61b. This white over-moulding acts as a reflector for the lens of the treatment surface, and hides internal parts in the cylindrical portion, which would include the battery 68 and control circuit 69.

The treatment surface 63 is shaped so as to cover, in use, the opening of the cervix, thus ensuring that the illumination from the LEDs is directed on to the treatment area. Treatment surface 63 comprises a contact surface 63a, which typically has a diameter of 22 to 30 mm. The contact surface 63a acts as a drug delivery system, i.e. drug carrying area or reservoir, and hence carries a composition comprising a photosensitiser or a precursor.

At the base of the cylindrical housing portion 61b a loop 64 is provided to facilitate insertion and removal of the device. A string can be attached to the loop 64, if required.

A preferred embodiment of the invention is shown in FIGS. 5 to 11. This example is for photodynamic treatment of the cervix. FIG. 5 shows the outer features of the moulded housing, which is made up of a first housing part 2 and a second housing part 4. The two housing parts are moulded from a resilient material, for example a medical grade silicone material. The first housing part 2 consists of a chamber 6 for holding a power source and an opening part 8 enabling access to the chamber 6 and for joining to the second housing part 4. The chamber 6 is generally cylindrical in this embodiment, reflecting the shape of the power source that it encases. The opening part 8 has two main parts, being a neck part 10 at the end of the chamber 6 and a coupling part 12 extending away from the neck part 10.

The second housing part 4 has a flexible outer portion 14 that, when moulded, forms a hollow frustoconical shape extending away from the first housing part 2 tapering outwardly away from the front of the device. When the device is in use the flexible outer portion 14 is folded back over the coupling part 12 of the first housing part 2 and hence forms a hollow frustoconical shape that tapers in the opposite direction, which would hence be tapering outwardly to the rear when the device is in use. In this context the rearward direction is the direction away from the cervix, out of the body, and the front of the device is the end of the device that faces toward the cervix with the forward direction in this embodiment hence being the direction in which light is emitted. It will be understood that the basic shape of the flexible outer portion 14 of the device of FIGS. 5 to 10, when in use, will be similar to the basic shape of the flexible outer portion 67 of the prior art device shown in FIGS. 1 to 4. Circumferential ribs 16 provide strength for the flexible outer portion 14 and also aid in the folding movement of the flexible outer portion 14 as it changes from the as-moulded shape (shown in FIG. 5) to the rearward tapering shape required for securing the device in the body.

Further detail of the device can be seen in the cross-section of FIG. 6. The first housing part 2 encloses a power source 41 in the form of a ½ AA sized lithium ion battery in the chamber 6. The battery 41 is held in an appropriate cradle 20, which also incorporates the required electrical connections for the battery 41. The chamber 6 is has a shape and size that is complementary to the shape and size of the battery 41 and cradle 20 and hence holds them tightly. In some embodiments the cradle may comprise a reed switch and an element such as a pin and the chamber 6 may comprise a notch (not shown). The notch will receive the pin and thus prevent a rotation of the cradle, i.e. rotation of the reed switch. This embodiment is preferred if the packaging of the device includes a magnet and where it needs to be ensured that the reed switch is held open while the device is inside the packaging. In some embodiments the chamber 6 may be moulded with a shape and size slightly smaller than the shape and size of the battery 41 and cradle 20 so that it is stretched around them via the resilience of the material of the first housing part 2. The battery 41 is electrically coupled to an LED lamp system 22 that is held on the second housing part 4. The LED lamp system 22 consists of LEDs 45 and a control circuit (described below with reference to FIG. 11) moulded on a circuit board 24.

Figure 7:
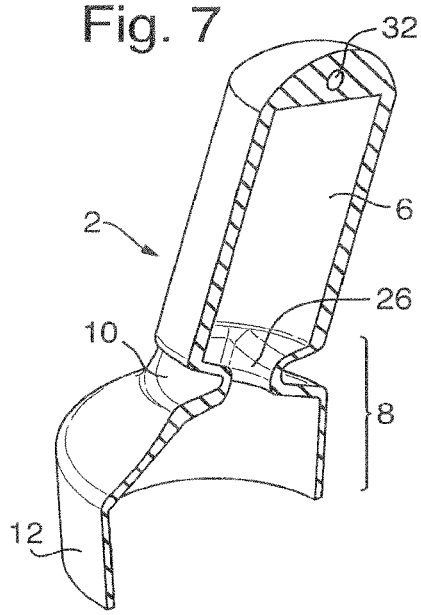
FIGS. 7 and 8 show a first housing part of the device of FIG. 5 in cut-away perspective view.
Figure 8:
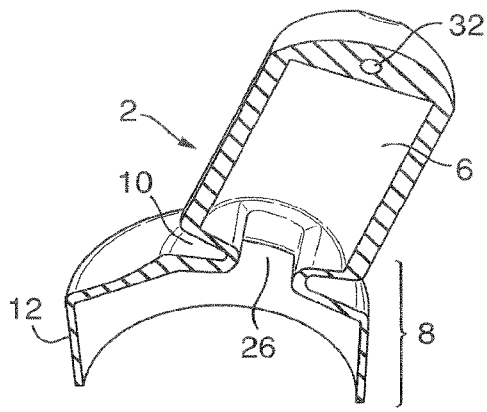

The electrical coupling for the LED lamp system 22 passes through the neck part 10, the details of which can be more clearly seen with reference to FIGS. 7 and 8. The neck part 10 has inner shoulders formed across the opening of the chamber 6 and outer shoulders across the width of the coupling part 12. The shoulders form a slot shaped hole 26, which is shown in transverse cross-section in FIG. 6. FIGS. 7 and 8 show one half of the slot shaped hole 26 with the first housing part 2 shown empty, omitting the battery 41 and cradle 20. The battery 41 and cradle 20 are inserted by deforming the resilient material of the first housing part 2 to stretch open the slot 26. When the battery 41 and cradle 20 are fully within the chamber 6 then the neck part 10 is allowed to return to its normal shape and the shoulders either side of the slot 26 hence hold the battery 41 and cradle 20 in place. It will be noted that the shape of the neck 10 also allows for the chamber 6 to bend along the line of the slot 26 so that it can move easily relative to the coupling part 12 and hence relative to the second housing part 4. This means that the device can deform whilst it is in use, making it more comfortable for the patient. FIGS. 7 and 8 also show the shape and form of the coupling part 12 effectively. In this example, since the device has a generally circular geometry for the second housing part 4, the coupling part 12 has a circular tube shaped section for joining to the second housing part 4. This circular tube section is attached to the outer shoulders of the neck part 10 by an asymmetric flange arrangement. The purpose of this is to make an angle between a central axis of the second housing part 4 and a central axis of the chamber 6 and battery 41 so that the device fits more comfortably within the body when in place for treatment of the cervix. Preferably, the first housing part 2 is moulded from a resilient material, preferably silicone. In a further preferred embodiment, the first housing part 2 is moulded from opaque silicone, i.e. the coupling part which will enclose the opening part 8 of the second housing part 4, once both housing parts 2 and 4 are joined together, is opaque to the light emitted by the LED lamp system 22, when the device is in use. In that way it is ensured that light emitted by the LED lamp system 22 only is emitted through the treatment surface 36 onto the cervix but not sideways onto the walls of the vagina.

Figure 9:
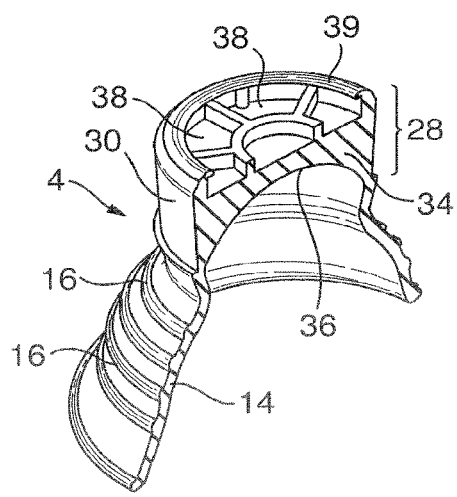
FIG. 9 shows a second housing part of the device of FIG. 5 in cut-away perspective view.

FIG. 9 shows the second housing part 4 which consists of the flexible outer portion 14 described above and a body and lens section 28. The first housing part 2 connects to the second housing part 4 via the coupling part 12 of the first housing part 2 and a corresponding coupling part 30 on the second housing part 4. In this example embodiment the coupling part 30 on the second housing part 4 is formed by the outer surface of the body and lens section 28, which has a cylindrical exterior. The two housing parts 2, 4 are joined by fitting the coupling part 12 of the first housing part 2 about the coupling part 30 on the second housing part 4. The resilient material of the coupling part 12 of the first housing part 2 can be stretched around the coupling part 30 on the second housing part 4 and will hence seal the device and securely hold the two housing parts 2, 4 together. The resilient fitting of the two coupling parts 12, 30 and the friction therebetween can be sufficient to keep the two housing parts 2, 4 together during use and form a fluid-tight seal. Optionally, however, a sealing and joining media such as an adhesive can be applied to ensure that the two housing parts 2, 4 cannot be separated during use of the device.

When in use the chamber 6 can be gripped to hold and manoeuvre the device and in addition a hole 32 though the rearward end of the chamber 6 allows for a cord to be attached to make it easier to remove the device from the body. Since the device will be pulled by the cord it is important to ensure that the first and second housing parts 2, 4 are securely attached together. When the device is removed in this way the flexible outer portion 14 of the second housing part 4 may unfold from its rearward tapering position to resume its as-moulded position. This would mean that the taper now faces forward, into the body cavity, resulting in a more comfortable and easier removal of the device.

FIGS. 9 and 10 illustrate the second housing part 4 and LED lamp system 22 in more detail in a perspective section view of the moulded housing part 4 alone and in a close up perspective section view of the body and lens section 28 with the LED lamp system 22 installed. The skirt-like flexible outer portion 14 has been described above. The body and lens section 28 has a cylindrical outer part forming the coupling part 30 and surrounding a solid lens 34, which is made of the resilient material. Since the resilient material used to mould the second housing part 4 is used to form the lens 34 then it should be at least partially transparent, as discussed above. The lens 34 has an outer treatment surface 36, which faces forward in use and is for placement against the cervix. Behind the lens 34 there are cavities 38 formed for holding elements of the LED lamp system 22. In this example the cavities 38 consist of six outer segments arranged symmetrically about an inner circular cavity. Each cavity can hold an LED 45 or LEDs 45 of the LED lamp system 22, which is mounted on a board 24 with a circular construction as seen in FIG. 10. The LEDs 45 hence direct light forward through the lens 34 and out via the treatment surface 36. Other components of the LED lamp system 22 are mounted on the rear face of the board 24. A lip 39 surrounds the rearward part of the lens and body section 28. This lip 39 is used to grip the outer circumference of the board 24 of the LED lamp system 22 and hence holds the LED lamp system 22 securely in position.

An alternative preferred form for the second housing part 4 is illustrated in FIGS. 11 and 12. FIG. 11 shows the second housing part 4 in a perspective view and FIG. 12 shows a similar view with the LED lamp system 22 fitted to the second housing part 4 and the cradle 20 attached to the LED lamp system 22. The features of this second housing part 4 are generally similar to the features described above with reference to FIGS. 9 and 10. It will however been seen that there is a significant change in relation to the arrangement of the cavities 38 that receive and hold elements of the LED lamp system 22. In this alternative form the cavities 38 are arranged to fit more closely to the LEDs 45 of the LED lamp system 22. This has advantages in preventing movement of the LED lamp system 22 when it is fitted to the second housing part 4 and also the closer fit of the LEDs 45 to the material of the housing part 4 can improve transmission of light to the treatment area on a patient as well as more effectively dissipating heat from the LEDs 45.

FIG. 12 shows the cradle 20 in the position that it would take when encased by the first housing part 2. The wires that connect the cradle 20 to the LED lamp system 22 would pass through the opening 26 in the first housing part 2 as described above.

During manufacture, the two housing parts 2, 4 are moulded of a silicone material. The battery 41 and cradle 20 is inserted into the chamber 6 as described above. The LED lamp system 22 is manufactured separately and is snap-fit into the second housing part 4, secured by the lip 39. The cavities 38 ensure that the LEDs 45 are consistently placed during manufacture. The battery 41 can then be electrically connected to the LED lamp system 22 and the two housing parts 2, 4 joined via the coupling parts. Any excess length in the wire or other electrical couplings used for the electrical connection can be coiled in the cavity at the rear of the LED lamp system 22.

Figure 13:
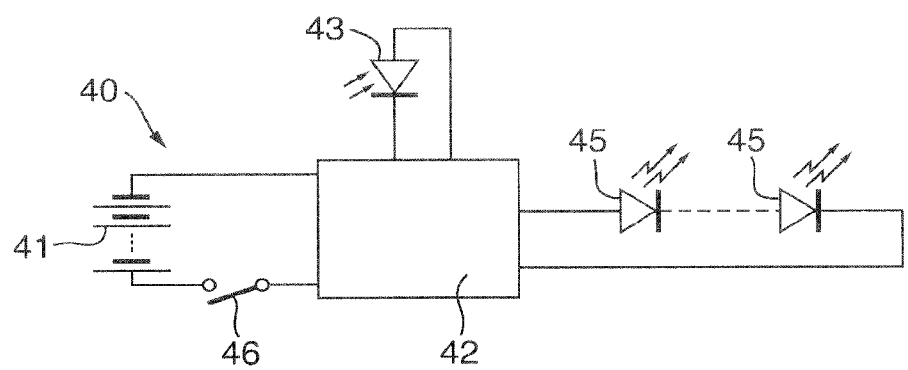
FIG. 13 shows a schematic diagram of a control circuit for use in the irradiation device of the preferred embodiments.

A control circuit suitable for use in any of the preferred embodiments of the irradiation device is shown in FIG. 13. This control circuit 40 takes power from one or more lithium batteries 41 that are used to power the LEDs 45. The control circuit 40 comprises a microprocessor 42, which controls the operation of the LEDs 45.

For example, the microprocessor 42 can comprise a timer and a memory into which can be programmed a dosage regime. The LEDs 45 can therefore be operated to illuminate the treatment area for a predetermined length of time and can be arranged to operate continuously or provide pulsed illumination. In addition the control circuit 40 comprises a light sensor 43. This forms a feedback circuit which enables the microprocessor 42 to adjust the operation of the LEDs 45 to ensure that any abnormalities or malfunction of the control circuit 40 do not affect the light dose received by the patient.

Prior to the insertion of the device, a switch 46 is closed to begin operation of the control circuit 40. This may, for example, initiate timing of a "delay period", after which the microprocessor 42 will begin operation of the LEDs 45 in accordance with the programmed treatment regime. After a predetermined time, or upon completion of delivery of a certain light dose (determined by light sensor 43) the microprocessor 42 will switch off the LEDs 45. The device can then be removed.

In modified embodiments the control circuit also comprises two operation indicator lights (not shown). These may comprise two LEDs, one of which is illuminated if the device has operated correctly and a second LED which is illuminated if any malfunction has occurred; combinations of lights may indicate specific faults. Alternatively only a single operation indicator light may be provided, which is illuminated upon completion of correct operation of the device and which remains unlit if any malfunction has occurred. The control circuit may incorporate an alarm device for providing an audible signal, and/or a vibration device for providing a signal by vibration.

This system alerts the patient and the medical practitioner if any malfunction has occurred which has prevented the patient from receiving the correct light dose. Signals from the control circuit can also indicate that the treatment has been completed successfully.

As discussed above, with a device intended for treatment of the cervix it is advantageous to provide different sizes since it allows effective treatment for patients with different histories of pregnancy. These different sizes can be realised by adjusting the size of the second housing part 4 and in particular the treatment surface 36 and the flexible skirt 14, as these portions act to secure the device within the vagina with the treatment surface placed against the cervix. The first housing part 2, which houses the power source 41, can then be manufactured in a single size, enabling a standardised arrangement to be used for the power source 41 and cradle 20. The cavities 38 and lip 39 can also be standardised in size allowing a single LED lamp system 22 to be fitted to second housing parts 4 that vary in the size of the treatment surface 36 and flexible outer portion 14.

However, it may be advantageous to vary the size of some elements of the first housing part 2, in particular the width of the slot 28 formed in the neck 10. The size of this part can be varied without changing the size of the chamber 6.

The composition comprising a photosensitiser or precursor for the photodynamic therapy can be applied to the patient prior to insertion of the device, either directly to the treatment area, or systematically, e.g. by intravenously or orally administered compositions. Preferably, the composition is applied to the treatment surface 36 so that the composition is applied to the patient during insertion of the device. With embodiments using a concave treatment surface, the composition may be placed within the concave area providing a reservoir of the composition as discussed above. Alternatively, the material of the device may be selected so that the composition will adhere to the treatment surface sufficiently for transfer to the patient and the composition can then be simply applied on the treatment surface.

Photodynamic Treatment of HPV Infections and Intraepithelial Neoplasia of the Cervix:

A composition comprising 5% by weight of the hydrochloride salt of ALA n-hexyl ester (hexaminolevulinate hydrochloride), a precursor of a photosensitiser, was prepared according to example 1 of WO 2010/142457. A device according to FIGS. 5-12 was used as a light source for the photodynamic treatment and was provided in a sealed plastic wrapping. The device contained LEDs which emit, when the device is in use, light at a wavelength of about 629 nm at a mean irradiance of about 7-8 mW/cm$^2$. A gynaecologist checked the operational status of the device followed by appropriate cleaning using disinfectant (e.g. alcohol). After cleaning the device, the gynaecologist applied 2 g of the composition onto the drug carrying area on the device. The composition was spread evenly over the surface of the drug carrying area using a spatula. Finally the gynaecologist inserted the device containing the composition into the vagina of a patient suffering from HPV infections and/or intraepithelial neoplasia of the cervix and positioned it correctly on the cervix. After insertion, the patients were allowed to leave the hospital at their convenience. The device delivered a total dose of about 125 J/cm$^2$ continuously for 4.6 hours after an initial delay of 5 hours, i.e. a total treatment time of 9.6 hours. The patients were told to not removed the device earlier than 10 hours after cervical administration, but within 24 hours (a cord was attached to the device to ensure easy removal) and to discard the removed device.

Determination of Irradiance

Irradiances from 7 LEDs 45 comprised in a LED lamp system 22 in devices according to FIGS. 5-12 were measured across the surface of the concave treatment surface 36 using an optical probe that was moved across the full area of treatment surface)(±50°. Irradiance was measured with the LED array in two orientations. The "across" profile corresponds to the measurement between the LEDs as shown in the schematic diagram on the left hand side of Error! Reference source not found. 14a while the "in line" profile is shown on the right hand side.

The measured irradiance profiles for device 1 are shown in FIG. 14b: the y-axis shows the irradiance measured in mW/cm$^2$ while the x-axis shows the angles in degrees. The diamond dotted line represents the measurements done with the "across profile" while the square dotted line represents the measurements done with the "in line" profile.

A summary of the maximum and minimum measurements for both profiles and calculation of the mean irradiance for each of the seven devices which were measured is shown below in Table 1.

TABLE 1

| Device no. | Max irradiance in line profile (mW/cm$^2$) | Min irradiance in line profile (mW/cm$^2$) | Max irradiance across profile (mW/cm$^2$) | Min irradiance across profile (mW/cm$^2$) | Mean irradiance (mW/cm$^2$) |
|---|---|---|---|---|---|
| 1 | 9.52 | 5.36 | 9.62 | 5.93 | 7.61 |
| 2 | 10.29 | 5.51 | 10.20 | 5.4 | 7.85 |
| 3 | 9.43 | 5.01 | 9.29 | 5.08 | 7.20 |

TABLE 1-continued

| Device no. | Max irradiance in line profile (mW/cm$^2$) | Min irradiance in line profile (mW/cm$^2$) | Max irradiance across profile (mW/cm$^2$) | Min irradiance across profile (mW/cm$^2$) | Mean irradiance (mW/cm$^2$) |
| --- | --- | --- | --- | --- | --- |
| 4 | 9.61 | 5.21 | 9.56 | 5.10 | 7.37 |
| 5 | 9.25 | 5.04 | 9.80 | 5.15 | 7.31 |
| 6 | 10.37 | 5.20 | 10.44 | 5.18 | 7.80 |
| 7 | 9.58 | 5.40 | 9.92 | 5.25 | 7.54 |

As will be appreciated, the device of the present invention provides a convenient way for photodynamic therapy to be carried out in any orifice of the human or animal body over long time periods and at low mean irradiance. This increases the convenience to the patient and may also increase the efficacy of the treatment.

The embodiments described above are for illustration only and should not be taken to limit the scope of protection. The skilled man will appreciate that adjustments could be made to these embodiments without deviating from the scope of the claims.

For example, the housing may be any shape which allows full and secure insertion into the orifice and the exact shape of this housing will depend on whether the device is intended for use on a human or animal subject and on the orifice where the treatment is to occur. In addition other forms of control circuit and LED lamp systems with other arrays of LEDs can be used within the invention. Also, although the preferred embodiment relates to a device for vaginal use and in particular for photodynamic treatment of diseases, lesions and conditions of the cervix, e.g. HPV infections and/or intraepithelial neoplasia, it will be understood that the same principles can be applied in the structure and manufacture of devices for other conditions and for use in other orifices, for example anal or oral devices.

Certain embodiments are as defined in the following numbered clauses:

1. An irradiation device for insertion into an orifice of the body to provide photodynamic therapy, the device comprising: a housing moulded from a resilient material and adapted to be fully inserted and secured in the orifice, the housing enclosing an LED lamp system and a power source for powering the LED lamp system; wherein the device is independently operational while located in the orifice; characterised in that: the housing comprises a first housing part for holding the power source and a second housing part for holding the LED lamp system, the first and second housing parts being separable and preferably being formed separately from the LED lamp system; and in that the first housing part consists of a chamber for holding the power source and an opening into the chamber is provided through a resilient opening part, wherein the chamber is closed when the first housing part is joined to the second housing part.

2. A device as defined in clause 1, wherein the resilient opening part allows for an electrical coupling to pass from the power source to the LED lamp system.

3. A device as defined in clause 1 or 2, wherein the resilient opening part can be deformed to insert and/or remove the power source into or from the first housing part.

4. A device as defined in clause 1 or 2, comprising a battery cap to provide an opening into the first housing part 5. A device as defined in clause 1, 2 or 3, wherein the resilient opening part comprises a neck part for holding the power source within the chamber.

6. A device as defined in clause 5, wherein the neck part is a resilient narrowing of the entrance to the chamber to a size less than the width of the power source to thereby hold the power source within the chamber.

7. A device as defined in any preceding clause, wherein the resilient material of the chamber is sized to fit tightly around the power source.

8. A device as defined in any preceding clause, wherein the power source and LED lamp system are arranged to permit the power source to be electrically connected to the LED lamp system whilst the first and second parts of the housing are separated from one another.

9. A device as defined in any preceding clause, wherein the power source is sealed within the housing such that the housing is fluid tight in use.

10. A device as defined in clause 9, wherein a sealing media is used at the joint between the first and second housing parts.

11. A device as defined in any preceding clause, wherein the resilient opening part has a coupling part arranged to join to and form a seal with a complementary shaped coupling part on the second housing part.

12. A device as defined in clause 11, wherein one of the two coupling parts is arranged to be stretched to place it around the other of the two coupling parts, thereby using the elasticity of the resilient material to hold the two housing parts together.

13. A device as defined in any preceding clause, wherein a part or all of the resilient material is at least partially transparent to light emitted from the LED lamp system, when the device is in use.

14. A device as defined in any preceding clause, wherein the second housing part to be moulded of a material that is at least partially transparent to light emitted from the LED lamp system when the device is in use, said light exits via a treatment surface on the second housing part and illuminates a treatment area on the patient and wherein the treatment surface has a size and/or shape adapted for complementary fit with said treatment area.

15. A device as defined in any preceding clause, wherein the second housing part has one or more moulded cavity to fit elements of the LED lamp system.

16. A device as defined in clause 15, wherein the one or more moulded cavity is enclosed by a fastening lip for securing elements of the LED lamp system within the cavity.

17. A device as defined in any preceding clause, wherein the device is adapted to be fully inserted and secured in the orifice and does not require connection to an external power supply or light source during operation.

18. A device as defined in any preceding clause, wherein, in use, the device provides light with a mean irradiance below 50 mW/cm$^2$.

19. A device as defined in any preceding clause, wherein the housing comprises a flexible outer portion that can adjust its shape to form a secure fit with the orifice 20. A device as defined in any preceding clause, wherein the flexible outer portion forms a continuous surface which tapers outwards towards the rear end of the device.

21. A device as defined in any preceding clause, further comprising a drug carrying area for carrying a composition comprising a photosensitizer or precursor of a photosensitizer.

22. A device as defined in clause 21 wherein the drug carrying area is the treatment surface.

23. A device as defined in clause 21 or 22 wherein the composition comprises a precursor which is 5-ALA, a derivative of 5-ALA or a pharmaceutically acceptable salt thereof, preferably 5-ALA or a precursor of formula (I) and pharmaceutically acceptable salts thereof:

$$R^2{}_2N\text{---}CH_2COCH_2\text{---}CH_2CO\text{---}OR^1 \quad (I)$$

wherein
$R^1$ represents a substituted or unsubstituted alkyl group; and $R^2$ each independently represents a hydrogen atom or a group $R^1$.

24. A device as defined in clause 24 wherein the composition comprises a precursor of formula (I) and pharmaceutically acceptable salts thereof, wherein $R^1$ is straight chain $C_1$-$C_6$ alkyl and both $R^2$ represent hydrogen.

25. A device as defined in clause 24 wherein the composition comprises 5-ALA hexyl ester or pharmaceutically acceptable salts thereof.

26. A kit comprising a device as defined in any of clauses 1 to 22 and at least one composition comprising a photo-sensitiser or precursor of a photosensitiser for use with the device.

27. A kit as defined in clause 26 wherein the composition comprises 5-ALA or a derivative of 5-ALA or a pharmaceutically acceptable salt thereof, preferably 5-ALA or a precursor of formula (I) and pharmaceutically acceptable salts thereof:

$$R^2{}_2N\text{---}CH_2COCH_2\text{---}CH_2CO\text{---}OR^1 \quad (I)$$

wherein
$R^1$ represents a substituted or unsubstituted alkyl group; and $R^2$ each independently represents a hydrogen atom or a group $R^1$.

28. A kit as defined in clause 27 wherein the composition comprises a precursor of formula (I) and pharmaceutically acceptable salts thereof, wherein $R^1$ is straight chain $C_1$-$C_6$ alkyl and both $R^2$ represent hydrogen.

29. A kit as defined in clause 28 wherein the composition comprises 5-ALA hexyl ester or pharmaceutically acceptable salts thereof.

30. A kit as defined in any preceding clause wherein said composition is provided separately from the device.

31. A kit as defined in any of clauses 26 to 29 wherein said composition is contained in the drug carrying area of the device.

32. A device or kit as defined in any preceding clause for use in photodynamic therapy, preferably the photodynamic therapy of abnormalities, diseases, lesions or conditions of the female reproductive system, preferably the vagina or the cervix.

33. A device or kit as defined in clause 32 for use in the photodynamic therapy of HPV infections, intraepithelial neoplasia, dysplasia, precancerous lesions and cancer of the female reproductive system, preferably the vagina and cervix.

34. A method of manufacturing an irradiation device for insertion into an orifice of the body to provide photodynamic therapy, the device comprising: a housing adapted to be fully inserted and secured in the orifice, the housing enclosing an LED lamp system and a power source for powering the LED lamp system; wherein the device is independently operational while located in the orifice; the method comprising: moulding a first housing part from a resilient material and moulding a second housing part from a resilient material, wherein the first housing part consists of a chamber for holding the power source and an opening into the chamber is provided through a resilient opening part, and the second housing part is for holding the LED lamp system, the first and second housing parts being separate mouldings and preferably being formed separately from the LED lamp system; and the method further comprising: closing the chamber by joining the first housing part to the second housing part in order to form the housing of the device.

35. A method of manufacturing as defined in clause 34 comprising providing features of the device or kit as defined in any of clauses 1 to 33.

36. A method of photodynamic therapy of a treatment area within an orifice of the body, the method comprising: applying a composition comprising a photosensitiser or precursor to the treatment area and using the device as defined in any of clauses 1 to 25 to provide illumination to treat the treatment area.

37. A method as defined in clause 36, comprising the photodynamic treatment of abnormalities, diseases, lesions or conditions of the female reproductive system, preferably the vagina and cervix.

38. A method as defined in clause 36 or 37, comprising the photodynamic treatment of HPV infections, intraepithelial neoplasia, dysplasia, precancerous lesions and cancer of the female reproductive system, preferably the vagina and cervix.

The invention claimed is:

1. An irradiation device for providing photodynamic therapy to the cervix, the device comprising:
    a housing comprising a separate first housing part for holding a power source for powering a LED lamp system, and a separate second housing part for holding the LED lamp system, wherein
    (a) the first housing part comprises:
        a chamber comprising the power source,
        an opening part to the chamber which comprises a first coupling part, and
        an electrical coupling passing from the power source to the LED lamp system in the second housing part; and
    (b) the second housing part comprises:
        a flexible outer portion which is frustoconical in shape that forms a continuous surface which tapers outwards towards the rear end of the device,
        a concave treatment surface,
        the LED lamp system, where the LED lamp system is arranged to emit light from the concave treatment surface onto the cervix, and
        a second coupling part;
    wherein the first coupling part on the first housing part is arranged to join to and form a seal with the second coupling part on the second housing part, thereby forming a joint and closing the chamber; and
    wherein the device, when in use, is fully inserted and secured in the vagina and is independently operational while located in the vagina.

2. The device as claimed in claim 1, wherein the first and second housing parts being formed separately from the LED lamp system.

3. The device as claimed in claim 1, wherein the first housing part is molded from a resilient material.

4. The device as claimed in claim 1, wherein the second housing part is molded from a resilient material.

5. The device as claimed in claim 1, wherein the first and the second housing parts are molded from a resilient material.

6. The device as claimed in claim 5, wherein the resilient material of the first housing part is sized to fit the chamber tightly around the power source.

7. The device as claimed in claim 6, wherein the power source is sealed within the housing such that the housing is fluid tight in use.

8. The device as claimed in claim 5, wherein one of the two coupling parts is arranged to be stretched to place it around the other of the two coupling parts, thereby using the elasticity of the resilient material to hold the two housing parts together.

9. The device as claimed in claim 5, wherein the second housing part is molded of a resilient material that is at least partially transparent to light emitted from the LED lamp system.

10. The device as claimed in claim 5, wherein the second housing part has one or more molded cavity to fit the LED lamp system.

11. The device as claimed in claim 10, wherein the one or more molded cavity is enclosed by a fastening lip for securing the LED lamp system within the cavity.

12. The device as claimed in claim 5, further comprising a drug carrying area for carrying a composition comprising a photosensitizer or precursor of a photosensitizer.

13. The device as claimed in claim 1, wherein a sealing media is used at the joint between the first coupling part and second coupling part.

14. The device as claimed in claim 1, wherein, in use, the device provides light with a mean irradiance below 50 mW/cm$^2$.

15. The device as claimed in claim 1, further comprising a drug carrying area for carrying a composition comprising a photosensitizer or precursor of a photosensitizer.

16. The device as claimed in claim 15, wherein the drug carrying area is the treatment surface on the second housing part.

17. The device as claimed in claim 16, wherein the composition comprises a precursor which is 5-ALA, a derivative of 5-ALA or a pharmaceutically acceptable salt thereof.

18. The device as claimed in claim 17, wherein the composition comprises 5-ALA hexyl ester or pharmaceutically acceptable salt thereof.

19. A kit comprising the device as claimed in claim 1 and at least one composition comprising a photosensitizer or precursor of a photosensitizer for use with the device.

20. The kit as claimed in claim 19, wherein the composition comprises 5-ALA hexyl ester or pharmaceutically acceptable salt thereof.

21. A kit comprising the device as claimed in claim 5 and at least one composition comprising a photosensitizer or precursor of a photosensitizer for use with the device.

22. A method of photodynamic therapy of the cervix, the method comprising: applying a composition comprising a photosensitizer or precursor to the cervix and using the device as claimed in claim 1 to provide illumination to the cervix.

23. The method as claimed in claim 22, wherein the composition comprises 5-ALA or a derivative of 5-ALA or a pharmaceutically acceptable salt thereof.

24. The method as claimed in claim 23, wherein the composition comprises 5-ALA hexyl ester or pharmaceutically acceptable salt thereof.

25. The method as claimed in claim 23, wherein the device comprises a drug carrying area, the composition is applied to the cervix via said drug carrying area and wherein the drug-carrying area is the treatment surface.

26. The method as claimed in claim 23, comprising the photodynamic treatment of abnormalities, diseases, lesions or conditions of the cervix.

27. The method as claimed in claim 26, comprising the photodynamic treatment of HPV infections, intraepithelial neoplasia, dysplasia, precancerous lesions and cancer of the cervix.

28. A method of photodynamic therapy of the cervix, the method comprising: applying a composition comprising a photosensitizer or precursor to the cervix and using the device as claimed in claim 5 to provide illumination to the cervix.

* * * * *